United States Patent
Nose Crotty et al.

(10) Patent No.: US 12,084,728 B2
(45) Date of Patent: Sep. 10, 2024

(54) INCREASING SEVERITY ACID HYDROLYSIS ASSAYS FOR DETERMINING THE AMOUNT OF GLUCOSE DERIVABLE FROM CELLULOSE IN FEEDSTOCKS

(71) Applicants: DANISCO US INC, Palo Alto, CA (US); ARCHER DANIELS MIDLAND COMPANY, Decatur, IL (US)

(72) Inventors: Kristin Y. Nose Crotty, Palo Alto, CA (US); Bradley R. Kelemen, Palo Alto, CA (US); Colin Fritz, Decatur, IL (US); Erin Rockafellow, Decatur, IL (US); Jacob Summerlott, Decator, IL (US)

(73) Assignees: Danisco US Inc., Palo Alto, CA (US); Archer Daniels Midland Company, Decatur, IL (US)

( * ) Notice: Subject to any disclaimer, the term of this patent is extended or adjusted under 35 U.S.C. 154(b) by 655 days.

(21) Appl. No.: 17/286,699

(22) PCT Filed: Oct. 14, 2019

(86) PCT No.: PCT/US2019/056071
§ 371 (c)(1),
(2) Date: Apr. 19, 2021

(87) PCT Pub. No.: WO2020/081432
PCT Pub. Date: Apr. 23, 2020

(65) Prior Publication Data
US 2021/0340638 A1    Nov. 4, 2021

Related U.S. Application Data

(60) Provisional application No. 62/747,443, filed on Oct. 18, 2018.

(51) Int. Cl.
*C12P 19/02* (2006.01)
*C12P 19/14* (2006.01)
(Continued)

(52) U.S. Cl.
CPC ............... *C13K 1/02* (2013.01); *C12P 19/02* (2013.01); *C12P 19/14* (2013.01); *C13K 1/06* (2013.01)

(58) Field of Classification Search
CPC ... C13K 1/02; C13K 1/06; C12P 19/02; C12P 19/14
See application file for complete search history.

(56) References Cited

U.S. PATENT DOCUMENTS

2017/0107547 A1 * 4/2017 Speetjens ................ A61P 37/02
2018/0258190 A1 * 9/2018 Balan ..................... C12P 19/14

OTHER PUBLICATIONS

Chio et al. "Two-step acid hydrolysis process kinetics in the saccharification of low-grade biomass: 1. Experimental studies on the formation and degradation of sugars," (Bioresource Technologies, vol. 58, Issue 2, Nov. 1996, pp. 101-106). (Year: 1996).*

(Continued)

*Primary Examiner* — Jill A Warden
*Assistant Examiner* — Michael Stanley Gzybowski

(57) ABSTRACT

Described are compositions and methods relating to the measurement of glucose derivable from the cellulosic components of a feedstock. The compositions and methods are particularly useful for ensuring that biofuel producers comply with the Renewable Fuel Standard while maximizing the value of the biofuel they produce.

18 Claims, 6 Drawing Sheets

[Cellulose] = [Total Glucan] - [Starch + Yeast β-Glucan]

(51) Int. Cl.
 *C13K 1/02* (2006.01)
 *C13K 1/06* (2006.01)

(56) References Cited

OTHER PUBLICATIONS

Choi et al. ("Two-Step Acid Hydrolysis Process Kinetics in the Saccharification of Low-Grade Biomass: 1. Experimental Studies of the Formation and Degradation of Sugars," Bioresource Technology 88, pp. 101-106, (1996)) (Year: 1996).*
Warren et al. ("The interplay of α-amylase and amyloglucosidase activities on the digestion of starch in in vitro enzymic systems," Carbohydr Polym. Mar. 6, 2015:117:192-200) (Year: 2015).*

* cited by examiner

INCREASING SEVERITY ACID HYDROLYSIS ASSAYS FOR DETERMINING THE AMOUNT OF GLUCOSE DERIVABLE FROM CELLULOSE IN FEEDSTOCKS

CROSS REFERENCE

The present application is a U.S. National Stage Application under 35 U.S.C. § 371 of International Patent Application No. PCT/US2019/056071, filed Oct. 14, 2019, which claims the benefit of U.S. Provisional Patent Application Ser. No. 62/747,443, filed Oct. 18, 2018, the contents of which are hereby incorporated by reference in their entirety.

TECHNICAL FIELD

The present compositions and methods relate to the precise and reliable measurement of the amount of glucose derivable from cellulosic components in a feedstock. The compositions and methods are particularly useful for ensuring that biofuel producers comply with the U.S. Environmental Protection Agency's Renewable Fuel Standard while maximizing the value of the biofuel they produce.

BACKGROUND

The Renewable Fuel Standard (RFS) is a federal program that requires a minimum volume of renewable fuels to be blended into transportation fuel sold in the United States. The RFS originated with the Energy Policy Act of 2005 and was extended and expanded in the Energy Independence and Security Act of 2007. In 2010, the Environmental Protection Agency (EPA) established a process for companies to petition for new fuel pathways to qualify for the (RFS) program. A fuel pathway is a specific combination of (1) a feedstock, (2) a production process and (3) a fuel type, wherein each combination of three components represents a separate fuel pathway. Qualifying fuel pathways are assigned one or more D-codes corresponding to the type of Renewable Identification Number (RIN) they are eligible to generate. Conventional renewable fuel (e.g., from corn) is D6, advanced biofuel is D5, biodiesel is D4 and cellulosic biofuel is D3 or D7. Cellulosic Biofuel (D-Codes 3 and 7) must be produced from cellulose, hemicellulose or lignin.

RINs are tradable regulatory credits that represent a quantity of qualifying renewable fuel. RINs are assigned after a producer reports the production of a gallon of fuel to the EPA. Blenders demonstrate compliance with the RFS by turning RINs over to the EPA once the gallon of fuel is blended into transportation fuel. Because the RFS requires increasing amounts of advanced biofuels (including cellulosic biofuels) as time progresses, RINs have different values depending on the fuel pathway from which they are generated. For example, a D3 RIN is currently worth more than a D6 RIN.

The current National Renewable Energy Laboratory (NREL) laboratory analytical procedure (LAP) for determination of structural carbohydrates and lignin in biomass is described by Sluiter, A. et al. ((2008) NREL Laboratory Analytical Procedure NREL/TP-510-42618. Golden, CO: National Renewable Energy Laboratory). The method is based on two-step acid hydrolysis, in which biomass is first hydrolyzed using 72 wt % sulfuric acid at 30° C. for 1 h, followed by dilution to 4 wt % sulfuric acid for further hydrolysis at 121° C. for 1 h under autoclave conditions. A faster, single-step method has been described in which biomass is hydrolyzed in 4 wt % sulfuric acid for further hydrolysis at 121° C. for 1 h under autoclave conditions (Gao, X. et al. (2014) *Biotechnology and Bioengineering* 111:1088-96). In both methods, the products of hydrolysis are analyzed by HPLC. A limitation of these methods is that they cannot distinguish glucose derived from starch as opposed to glucose derived from cellulose and, therefore cannot be used to determine the fraction of glucose derived from cellulose in a mixed starch-cellulose feedstock. The EPA established corn kernel fiber as a qualified crop residue on Jul. 18, 2014.

As corn ethanol producers attempt to utilize corn fiber, as well as corn starch, to produce ethanol, there is a financial incentive to characterize as much ethanol as possible as D3 biofuel. However, the EPA requires accuracy in accounting and producers that have non-accurately characterized their biofuel can be subject to penalties. Accordingly, the need exists for an accurate method for determining the source of ethanol when mixed feedstocks of starch and cellulosic components are used to produce biofuels.

SUMMARY

Described are compositions and methods relating to measurement of the amount of glucose derivable from the cellulosic components of a feedstock. Aspects and embodiments of the compositions and methods are described in the following, independently-numbered paragraphs.

1. In one aspect, a method for measuring the amount of cellulose-derivable glucose in a feedstock comprising a mixture of starch and cellulosic components is provided, comprising: determining the amount of glucose present in a first portion of the feedstock contacted with about 30 to about 55 wt % sulfuric acid for about 1 hour, optionally at about 30° C., followed by diluting the first portion of the feedstock to 2 wt % sulfuric acid and continuing incubation for about 45 minutes under autoclave conditions compared to a second portion of the feedstock contacted with about 63-83 wt % sulfuric acid for about 1 hour at about 30° C. followed by diluting the second portion of the feedstock to 4 wt % sulfuric acid and continuing incubation for about 45 minutes under autoclave conditions; where increased glucose in the second portion of the feedstock contacted with 63-83 wt % sulfuric acid compared to the first portion of the feedstock contacted with about 30 to about 55 wt % sulfuric acid corresponds to glucose derived from cellulose in the feedstock.

2. In another aspect, a method for measuring the amount of cellulose-derivable glucose in a feedstock comprising a mixture of starch and cellulosic components is provided, comprising: (i) contacting a first portion of the feedstock with about 30 to about 55 wt % sulfuric acid for about 1 hour, optionally at about 30° C., followed by diluting the first portion of the feedstock to 2 wt % sulfuric acid and continuing incubation for about 45 minutes under autoclave conditions; (ii) contacting a second portion of the feedstock with about 63-83 wt % sulfuric acid for about 1 hour at about 30° C. followed by diluting the second portion of the feedstock to 4 wt % sulfuric acid and continuing incubation for about 45 minutes under autoclave conditions; (iii) cooling the first and second portions of the feedstock contacted with sulfuric acid in (i) and (ii) and neutralizing acidity with calcium carbonate; and (iv) determining the amount of glucose present in the first and second portions of the feedstock contacted with sulfuric acid in (i) and (ii), where increased glucose in the second portion of the feedstock contacted with sulfuric acid in (ii) compared the first portion of the feedstock contacted with sulfuric acid in (i) corresponds to glucose derived from cellulose.

3. In some embodiments of the method of paragraph 1 or 2, the first portion of the feedstock is contacted with about 36-45 wt % sulfuric acid.

3. In some embodiments of the method of any of paragraphs 1-3, the second portion of the feedstock is contacted with about 72 wt % sulfuric acid.

5. In another aspect, a method for measuring the amount of cellulose-derivable glucose in a feedstock comprising a mixture of starch and cellulosic components is provided, comprising: determining the amount of glucose present in sample of the feedstock contacted with about 63-83 wt % sulfuric acid for about 1 hour at about 30° C. followed by diluting the sample of the feedstock to 4 wt % sulfuric acid and continuing incubation for about 45 minutes under autoclave conditions, from which sample soluble material obtained by contacting the sample with about 30 to about 55 wt % sulfuric acid for about 1 hour, optionally at about 30° C., followed by diluting the sample of the feedstock to 2 wt % sulfuric acid and continuing incubation for about 45 minutes under autoclave conditions has previously been removed, where amount of glucose in the sample of the feedstock contacted with 72 wt % sulfuric acid corresponds to glucose derived from cellulose in the feedstock.

6. In another aspect, a method for measuring the amount of cellulose-derivable glucose in a feedstock comprising a mixture of starch and cellulosic components is provided, comprising: (i) contacting a sample of the feedstock with about 30 to about 55 wt % sulfuric acid for about 1 hour, optionally at about 30° C., followed by diluting the sample of the feedstock to 2 wt % sulfuric acid and continuing incubation for about 45 minutes under autoclave conditions; (ii) removing soluble material from the sample of the feedstock; (iii) contacting the remaining material in the sample of the feedstock with about 63-83 wt % sulfuric acid for about 1 hour at about 30° C. followed by diluting the sample of the feedstock to 4 wt % sulfuric acid and continuing incubation for about 45 minutes under autoclave conditions; (iv) cooling the sample of the feedstock contacted with sulfuric acid in (iii) and neutralizing acidity with calcium carbonate; and (v) determining the amount of glucose present in the sample the feedstock contacted with sulfuric acid in (iii), where glucose in the sample of the feedstock contacted with sulfuric acid in (iii) corresponds to glucose derived from cellulose.

7. In some embodiments of the method of paragraph 6, the feedstock contains yeast cells and prior to step (iii) the remaining material is contacted with a lyticase enzyme at a temperature and for a time sufficient to release glucans from yeast present in the sample.

8. In some embodiments of the method of paragraph 7, after contacting with the lyticase the sample is separated into a solubles liquid fraction and a solids fraction and the solids fraction is washed to remove residual solubles prior to contacting with about 63-83 wt % sulfuric acid.

9. In some embodiments of the method of any of paragraphs 6-8, the sample of the feedstock is contacted with about 36-45 wt % sulfuric acid in (i).

10. In some embodiments of the method of any of paragraphs 6-9, the sample of the feedstock is contacted with about 72 wt % sulfuric acid in (iii).

11. In some embodiments of the method of any of paragraphs 1-10, the feedstock is dried prior to being contacted with sulfuric acid.

12. In some embodiments of the method of any of paragraphs 1-11, the feedstock is washed with isopropanol prior to being contacted with sulfuric acid.

13. In some embodiments of the method of any of paragraphs 1-12, the amount of glucose derived from cellulose is used to determine the amount of cellulosic ethanol derivable from a feedstock.

14. In another aspect, a kit of parts for measuring the amount of cellulose-derivable glucose in a feedstock is provided, comprising a mixture of starch and cellulosic components, comprising: (i) autoclavable sample tubes, (ii) a solution of sulfuric acid at a concentration such that, when added to a first portion of feedstocks at a predetermined volume ratio is sufficient to produce a first portion of the feedstock having about 30 to about 55 wt % sulfuric acid and (iii) a solution of sulfuric acid at a concentration such that, when added to a second portion of feedstocks at a predetermined volume ratio is sufficient to produce a second portion of the feedstock having 63-83 wt % sulfuric acid and (iv) instructions for use.

15. In some embodiments of the kit of parts of paragraph 14, the solution of sulfuric acid in (ii) is at a concentration sufficient to produce first portion of feedstock having about 36-45 wt % sulfuric acid.

16. In some embodiments of the kit of parts of paragraph 14 or 15, the solution of sulfuric acid in (iii) is at a concentration sufficient to produce first portion of feedstock having about 72 wt % sulfuric acid.

17. In another aspect, a kit of parts for measuring the amount of cellulose-derivable glucose in a feedstock is provided, comprising a mixture of starch and cellulosic components, comprising: (i) autoclavable sample tubes, (ii) a solution of sulfuric acid at a concentration such that, when added to a sample of feedstocks at a predetermined volume ratio is sufficient to produce sample of the feedstock having about 30 to about 55 wt % sulfuric acid and (iii) a solution of sulfuric acid at a concentration such that, when added to the sample of the feedstock at a predetermined volume ratio or amount is sufficient to produce a sample of the feedstock having 63-83 wt % sulfuric acid and (iv) instructions for use.

18. In some embodiments of the kit of parts of paragraph 17, the solution of sulfuric acid in (ii) is at a concentration sufficient to produce a sample of feedstock having about 36-45 wt % sulfuric acid.

19. In some embodiments of the kit of parts of paragraph 17 or 18, the solution of sulfuric acid in (iii) is at a concentration sufficient to produce a sample of feedstock having about 72 wt % sulfuric acid.

20. In some embodiments, the kit of parts of any of paragraphs 16-19, further comprises a column for high performance liquid chromatography.

21. In another aspect, a method for measuring the amount of cellulose-derivable glucose in a feedstock is provided, comprising a mixture of starch and β-glucan and hemicellulose components, comprising: (i) contacting a sample of the feedstock with a 2 to 4-molar hydroxide base at a temperature of −5 to 5° C. for at least 10 minutes then adding a buffer to bring the sample to a pH is suitable for operation of amyloglucosidase and α-amylase enzymes; (ii) contacting the feedstock with amyloglucosidase and an α-amylase at a temperature of 90 to 100° C. for a time sufficient to enzymatically hydrolyze at least 90% of the starch to glucose forming a first solubles fraction; (iii) separating the first solubles fraction from solids present in the feedstock and retaining a first separated solids fraction; (iv) determining the amount of glucose present in the first solubles fraction, which corresponds to starch derived glucose; (v) contacting the retained solids fraction with sulfuric acid at a concentration of 63-83% at a temperature of 27-33° C. for a time of 55-65 minutes forming a concentrated acid treated sample; (vi) diluting the sulfuric acid in the concentrated acid treated sample to 4% forming a diluted acid sample; (vii) incubating the diluted acid sample at temperature of 120-121° C. under autoclave conditions for a time sufficient to chemically hydrolyze at least 90% of the cellulosic components initially present in the feedstock to glucose forming a second solubles liquid fraction; (viii) separating the second solubles fraction from a second solids fraction obtained from the diluted acid sample; and (ix) determining the amount of glucose present in the second solubles fraction, which corresponds to the cellulosic derived glucose.

22. In some embodiments of the method of paragraph 21, the sample of the feedstock is contacted with about 72 wt % sulfuric acid in (v).

23. In some embodiments of the method of paragraph 21 or 22, the feedstock contains yeast cells, and wherein prior to step (v) the feedstock is contacted with a lyticase enzyme at a temperature of 45-55° C. for a time sufficient to hydrolyze at least 90% of yeast β-glucans in the sample.

24. In some embodiments of the method of any of paragraphs 21-23, the feedstock is washed with an isopropyl alcohol prior to step (i).

25. In some embodiments of the method of any of paragraphs 21-24, the first retained solids fraction is washed to remove residual solubles material prior to step (v).

26. In another aspect, a method for reducing the interference of yeast cells when analyzing a sample feedstock for the release of glucose from starch and/or cellulosic components in the feedstock is provided, comprising contacting a sample of the feedstock containing starch and/or cellulosic components and yeast with a lyticase enzyme with an amount of a lyticase enzyme at a temperature and for a time sufficient to hydrolyze at least 90% of yeast β-glucans present in the sample prior to analyzing the sample feedstock for the release of glucose from the starch and/or cellulosic components in the feedstock.

27. In some embodiments of the method of paragraph 26, the solids sample contacted with the lyticase is washed to remove residual solubles materials prior to analyzing the sample feedstock for the release of glucose from the starch and/or cellulosic components.

These and other aspects and embodiments of present compositions and methods will be apparent from the description and drawings.

DETAILED DESCRIPTION

I. Overview

Figure 1:
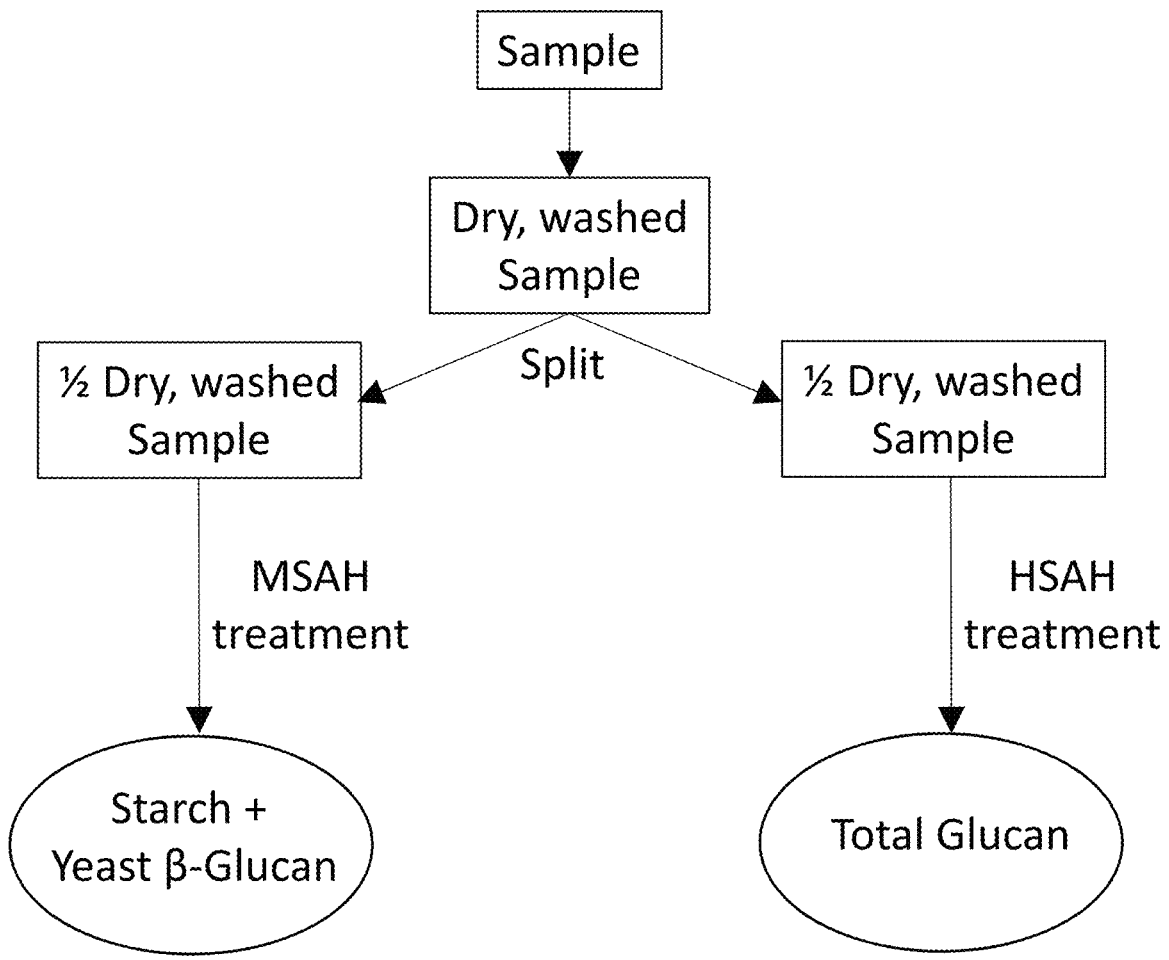
FIG. 1 is a flowchart illustrating the VSAH method.

The present compositions and methods are based on the ability to precisely and reliably measure the amount of glucose derived or derivable from cellulosic components of a feedstock, including a mixed starch/cellulosic feedstock. The compositions and method provide a way for ethanol producers to accurately assign D3 RINs to a portion of the ethanol produced by a fuel ethanol plant. The compositions and methods are sufficiently inexpensive and simple to use that they can be used for routine feedstock analysis as feedstocks vary throughout the year, or even for every feedstock used in an ethanol production facility.

In some embodiments, the compositions and methods involve only simple chemical treatment of samples followed by analytical analysis. In other embodiments, the compositions and methods involve a hybrid enzymatic-chemical treatment of samples followed by analytical analysis. Both methods produce excellent results in terms of distinguishing glucose obtainable from cellulosic materials from glucose obtainable from starch.

II. Definitions

Prior to describing the present methods in detail, the following terms are defined for clarity. Terms not defined should be accorded their ordinary meanings as used in the relevant art.

As used herein, "cellulose" refers to a polysaccharide consisting of a linear chain of β(1,4)-linked D-glucose units with the formula $(C_6H_{10}O_5)_n$, wherein "n" can be any integer greater than or equal to two. Cellulose is a key structural component of plants.

As used herein, "starch" refers to a polysaccharide consisting of a linear chain of α-1,4-linked D-glucose units with the formula $(C_6H_{10}O_5)_n$, wherein "n" can be any integer greater than or equal to two. Starch is abundant in grains, grasses, tubers and roots, and more specifically wheat, barley, corn, rye, rice, sorghum, brans, cassava, millet, potato, sweet potato, and tapioca.

As used herein, a "feedstock" is a starting substrate for hydrolysis (typically enzymatic) to obtain glucose, which can optionally be used to produce valuable chemicals, such as citric acid, lactic acid, succinic acid, monosodium glutamate, gluconic acid, sodium gluconate, calcium gluconate, potassium gluconate, itaconic acid and other carboxylic acids, glucono delta-lactone, sodium erythorbate, lysine and other amino acids, omega 3 fatty acid, butanol, isoprene, 1,3-propanediol, pyruvate, 2,3-butanediol and other biomaterials, and alcohols, such as ethanol and butanol.

As used herein, the term "lyticase" refers to endoglucanase and protease activities that act together in yeast cell lysis as described in, e.g., Scott, J. H. and Schekman, R. (1980) *J. Bacteriol.* 142:414-23.

As used herein, a "slurry" is a semiliquid mixture of fine particles suspended in water or another solvent.

As used herein, "contacting" a feedstock with an acid refers to bringing the feedstock and acid together in a common aqueous environment, typically accompanied by mixing to achieve uniform distribution. The term "contacted" is used interchangeably with "treated."

As used herein, an "ethanologenic microorganism" refers to a microorganism with the ability to convert a sugar or oligosaccharide to ethanol.

As used herein, the term about, with respect to the acid concentration for VSAH conditions refers to ±1 wt %, ±2 wt %, ±3 wt %, ±4 wt %, but no more than ±5 wt % of the stated acid concentration.

As used herein, the term about, with respect to the temperatures for VSAH conditions refers to ±1° C., ±2° C., ±3° C., ±4° C., but no more than ±5° C. of the stated temperature.

As used herein, the term about, with respect to the times for VSAH incubations refers to ±4 minutes, ±6 minutes, ±8 minutes, but no more than ±10 minutes of the stated time.

As used herein, the term about, with respect to the pressure for VSAH incubations refers to ±5 kPa, ±10 kPa, ±15 kPa, but no more than ±20 kPa of the stated pressure.

As used herein, atmospheric pressure is 0 kPa (gauge).

As used herein, autoclave conditions are generally 121° C. and 100 kPa (gauge).

As used herein, the singular articles "a," "an" and "the" encompass the plural referents unless the context clearly dictates otherwise. All references cited herein are hereby incorporated by reference in their entirety. The following abbreviations/acronyms have the following meanings unless otherwise specified:

| | |
|---|---|
| ° C. | degrees Centigrade |
| EHSAH | enzyme hydrolysis high severity acid hydrolysis |
| g or gm | grams |
| HPLC | high performance liquid chromatography |
| hr(s) | hour/hours |
| HSAH | high severity acid hydrolysis |
| IPA | isopropyl alcohol |
| kg | kilograms |
| kPa | kiloPascals |
| M | molar |
| mg | milligrams |
| min(s) | minute/minutes |
| mL and ml | milliliters |
| mm | millimeters |
| mM | millimolar |
| MSAH | medium severity acid hydrolysis |
| NREL | National Renewable Energy Laboratory |
| RCF | relative centrifugal force |
| SEHSAH | serial enzyme hydrolysis high severity acid hydrolysis |
| SISAH | serial increasing severity acid hydrolysis |
| SRS | sugar recovery standards |
| VSAH | variable severity acid hydrolysis |
| wt % | weigh percent |
| μg | micrograms |
| μL and μl | microliters |
| μm | micrometer |
| μM | micromolar |
| VSCB | voluntary standard consensus body |

III. Variable Severity Acid Hydrolysis Assay

In a first embodiment of the compositions and methods variable severity acid hydrolysis (VSAH) conditions are used to hydrolyze starch and cellulose present in feedstocks to glucose. The process is summarized in the flowchart in FIG. 1. While cellulose and starch are known to have differential resistance to acid hydrolysis, it was heretofore unknown that the use of specific hydrolysis conditions could be used to quantitatively distinguish glucose derived from cellulose from glucose derived from starch. As fermentation organisms that produce ethanol (i.e., ethanologens) are agnostic to the origin of the glucose that they metabolize, determining the amount of cellulose-derivable glucose (and resulting end products) in a feedstock has thus proven difficult.

Central to this embodiment of the compositions and methods is the treatment of the feedstock with at least two different amounts of acid. While numerous acids may be employed in the compositions and methods, the preferred acid is sulfuric acid. Treatment with sulfuric acid is performed under two conditions: (i) medium severity acid hydrolysis (MSAH) and (ii) high severity acid hydrolysis (HSAH).

MSAH is initially performed at a sulfuric acid concentration of about 30-55 wt %, or about 36-45 wt % (final concentration), of diluted feedstock for about an hour at about 30° C., at atmospheric pressure. Agitation is preferred but not required. The type of vessel is not critical but should generally be air and water-tight at 30° C. Following the 1-hour incubation, the feedstock is diluted with an aqueous solution (generally, water) to a sulfuric acid concentration of about 2 wt % of diluted feedstock and incubation is continued for about 45 minutes under autoclave conditions, which are generally 121° C. and 100 kPa. Agitation is not required but a pressure tube should be used to avoid sample loss.

HSAH is initially performed at a sulfuric acid concentration of about 63-83 wt %, and in some cases 72 wt %, (final concentration) of diluted feedstock for about an hour at about 30° C., at atmospheric pressure. Agitation is preferred but not required. As before, the type of vessel is not critical but should generally be air and water-tight at 30° C. Following the 1-hour incubation, the feedstock is diluted with an aqueous solution (generally, water) to a sulfuric acid concentration of about 4 wt % of diluted feedstock and incubation is continued for about 45 minutes under autoclave conditions in a pressure tube.

The amounts of acid, the incubation times and the temperature and pressure conditions are selected for the most quantitative separation of glucose derived from cellulose and glucose derived from starch, while using common laboratory equipment, such as a water bath, an autoclave and HPLC analysis equipment. Minor changes in the incubation conditions may give acceptable results in terms of accuracy and reproducibility but they are not recommended to ensure the best results and consistency across the industry.

While the important part of the reaction is the VSAH treatment, attention should also be given to sample preparation for glucose analysis. The samples are preferably cooled for practical reasons and neutralized with, e.g., calcium carbonate to stop the reactions. Other neutralizing composition can be used, so long as they do not interfere with analysis.

Samples may be analyzed by various chromatographic techniques; however, since accuracy is a primary objective in development of the present compositions and methods, HPLC analysis is preferred. Organic acids columns are well suited for the separation of glucose from other monosaccharides. It will be appreciated that while other starch, cellulose and even xylose acid hydrolysis products may be analyzed using the present compositions and methods, only the relative amounts of glucose in the MSAH and HSAH treated samples are critical.

IV. Serial Increasing Severity Acid Hydrolysis Assay

Figure 2:
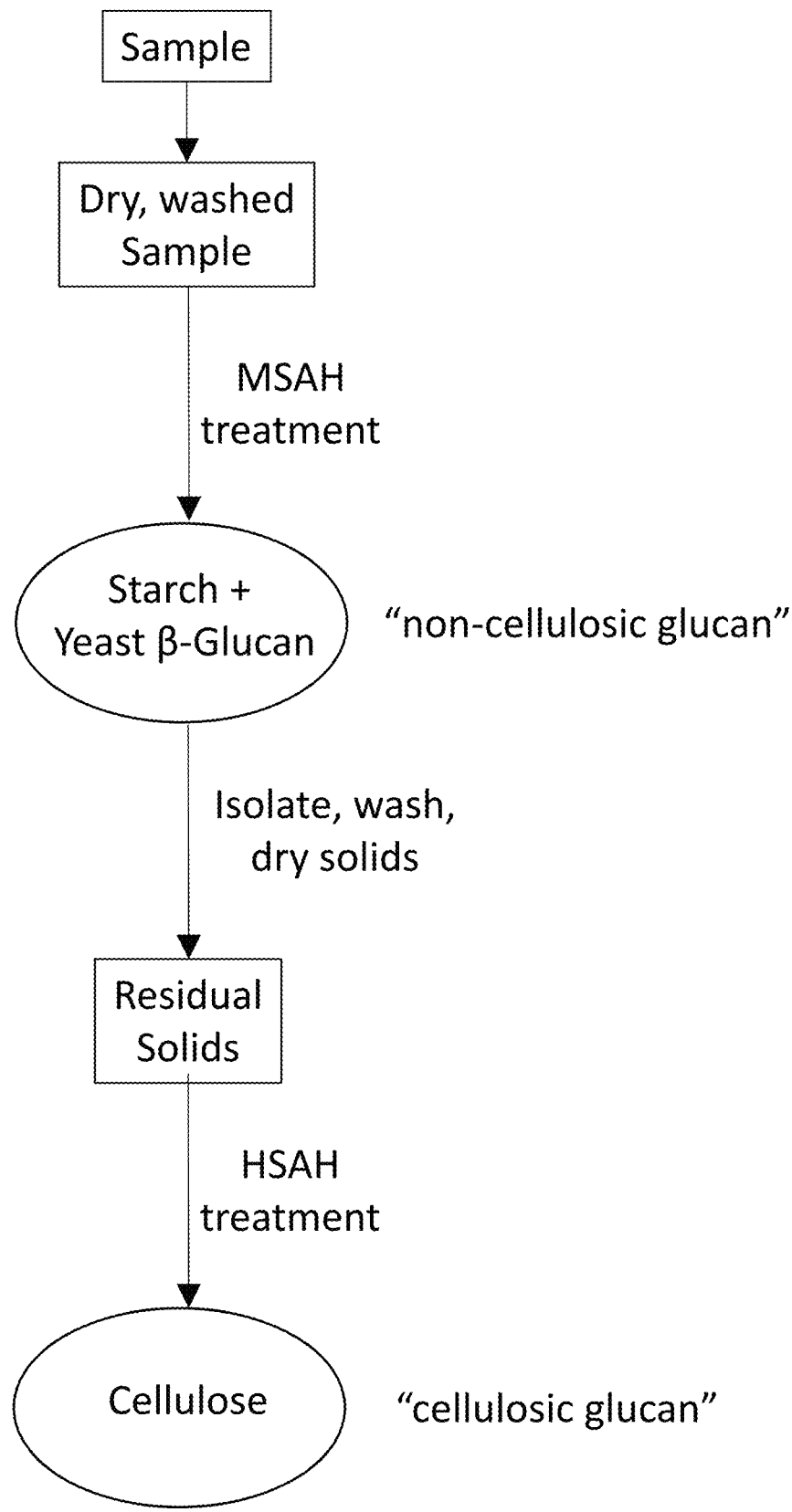
FIG. 2 is a flowchart illustrating the SISAH method.

A second embodiment of the compositions and methods is a variation of VSAH involving serial increasing severity acid hydrolysis (SISAH) conditions to hydrolyze starch and cellulose present in feedstocks to glucose. The process is summarized in the flowchart in FIG. 2. In this embodiment of the compositions and methods, VSAH and HSAW are performed sequentially rather than separately.

As before, MSAH is initially performed at a sulfuric acid concentration of about 30-55 wt %, or about 36-45 wt % (final concentration) of diluted feedstock for about an hour at about 30° C., at atmospheric pressure, and agitation is preferred but not required. The type of vessel is not critical but should generally be air and water-tight at 30° C. Following the 1-hour incubation, the feedstock is diluted with an aqueous solution (generally, water) to a sulfuric acid concentration of about 2 wt % of diluted feedstock and incubation is continued for about 45 minutes under autoclave conditions, which are generally 121° C. and 100 kPa. As before, agitation is not required but a pressure tube should be used to avoid sample loss.

Following treatment under MSAH conditions, soluble material containing glucose derived from starch is separated from insoluble material containing cellulose, e.g., by centrifugation. The insoluble material may be washed with most any aqueous solution other than those meeting HSAH conditions. The remaining material is then subjected to HSAH treatment. This may conveniently be performed in the same vessel.

HSAH is initially performed at a sulfuric acid concentration of about 63-83 wt %, and in some cases 72 wt %, (final concentration) of diluted feedstock for about an hour at about 30° C., at atmospheric pressure. Agitation is preferred but not required. As before, the type of vessel is not critical but should generally be air and water-tight at 30° C. Following the 1-hour incubation, the feedstock is diluted with an aqueous solution (generally, water) to a sulfuric acid concentration of about 4 wt % of diluted feedstock and incubation is continued for about 45 minutes under autoclave conditions in a pressure tube.

The amounts of acid, the incubation times and the temperature and pressure conditions are selected for the most quantitative separation of glucose derived from cellulose and glucose derived from starch, while using common laboratory equipment, such as a water bath, an autoclave and HPLC analysis equipment. Minor changes in the incubation conditions may give acceptable results in terms of accuracy and reproducibility but they are not recommended to ensure the best results and consistency across the industry.

While the important part of the reaction is the SISAH treatment, attention should also be given to sample preparation for glucose analysis. The samples are preferably cooled for practical reasons and neutralized with, e.g., calcium carbonate to stop the reactions. Other neutralizing composition can be used, so long as they do not interfere with sample preparation or analysis.

As is the case for VSAH samples, SISAH samples may be analyzed by various chromatographic techniques; however, since accuracy is a primary objective in development of the present compositions and methods, HPLC analysis is preferred. Organic acids columns are well suited for the separation of glucose from other monosaccharides. It will be appreciated that while other starch, cellulose and even xylose acid hydrolysis products may be analyzed using the present compositions and methods, only the amounts of glucose in the SISAH treated samples are critical.

V. Hybrid Enzyme-Chemical High Severity Acid Hydrolysis

Voluntary standard consensus body (VSCB) methods use enzymes to selectively hydrolyze total starch. Other VSCB methods use acid hydrolysis to target total glucans. National Renewable Energy Laboratory (NREL) recommends separating liquid and solids of pretreated biomass (developed for non-starch containing materials) for compositional analysis (Sluiter, J. and Sluiter, A. *Summative Mass Closure*. Technical Report, NREL/TP-510-48825). August 2010. Unfortunately, when combining VSCB methods with NREL separations with high starch/low cellulose feedstocks, such as are present in an ethanol fermentation slurry, these methods do not produce cellulose measurements with sufficient precision required to measure cellulosic contribution to in situ fermentations.

Figure 3:
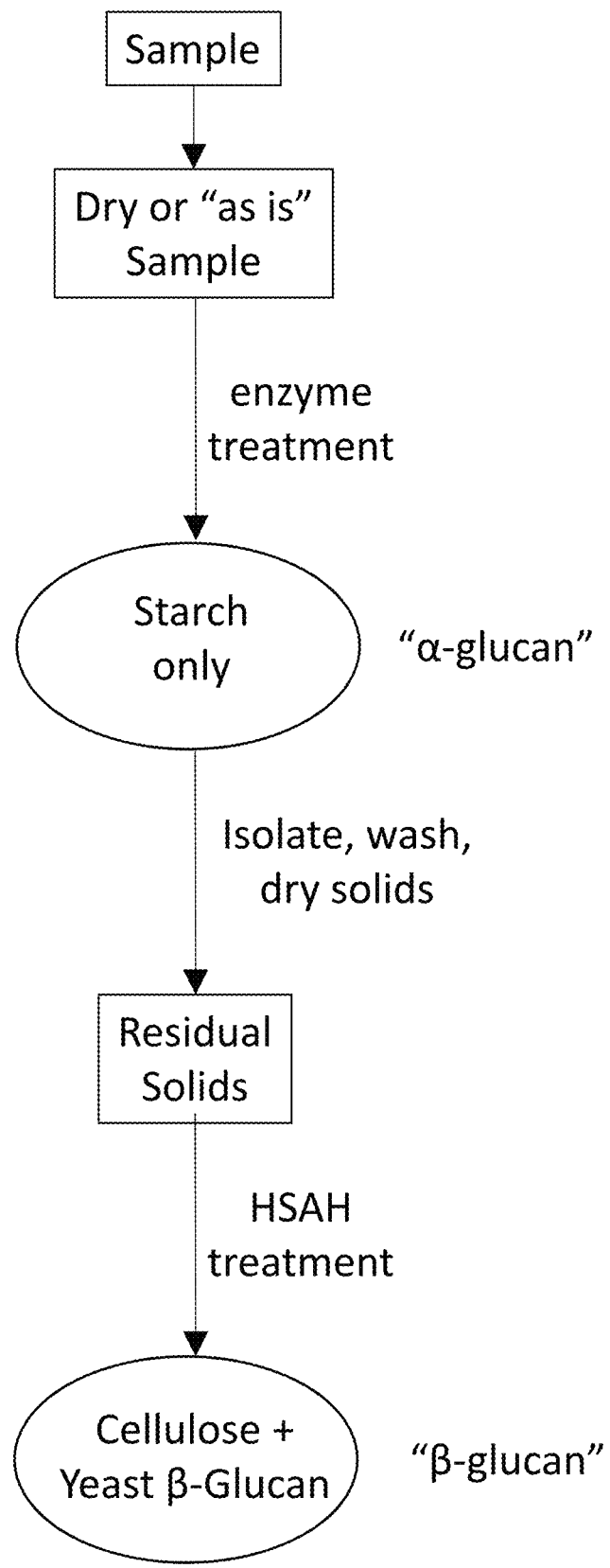
FIG. 3 is a flowchart illustrating the SEHSAH method.

As an alternative to using SISAH methods for determining the amount of glucose released from starch versus the cellulosic components in a feedstock, a hybrid serial method that combines enzymatic hydrolysis followed by high severe acid hydrolysis (SEHSAH) may also be employed for the same purpose with highly reproducible results. The process is summarized in the flowchart in FIG. 3. In this embodiment of the compositions and methods, an enzyme cocktail that includes amyloglucosidase in combination with α-amylase is first used to hydrolyze the starch component of the feedstock to glucose forming a first soluble material fraction that is separated from solids remaining in the sample using filtration, centrifugation or other suitable means. The amount of glucose present in the first soluble material fraction is entirely derived from starch because the enzyme cocktail contains starch degrading enzymes but lacks sufficient β-glucosidases, cellobiohydrolases or other cellulosic degrading enzymes to degrade the cellulosic materials. The separated insoluble solids fraction, on the other hand, contains the un-hydrolyzed β-glucans constituting the cellulosic component. This insoluble solids fraction is subsequently subjected to HSAH conditions, as described above for use in the VSAH and SISAH embodiments, to determine the amount of glucose released from the cellulosic components of the feedstock using the SEHSAH method.

Prior methods of using enzymatic hydrolysis of starch in a mixed feedstock also containing cellulosic material were subject to inaccuracy and variability in results. It has been determined that such inaccuracy and variability arises from the steric inability of the starch hydrolyzing enzymes to reach all available starch components in the feedstock because some starch polymer is bound up with other starch polymers and cellulosic material through ester bonds and/or through non-covalent physical intertwining.

A remedy to this problem is to contact the feedstock with a hydroxide salt with mechanical agitation for a period of time and a temperature sufficient to hydrolyze ester bonds and mechanically dislodge non-covalently intertwined starch without causing base catalyzed hydrolysis of the starch polymer. Any basic hydroxide salt may be used, including but not limited to sodium, potassium and ammonium hydroxide. In exemplary embodiments potassium hydroxide was used. The feedstock should be contacted with the hydroxide salt at a hydroxide concentration between 1.5 and 2.5 M molar in the sample. In exemplary embodiments the hydroxide concentration was 2 M. To minimize base hydrolysis of glycoside bonds, the contacting is performed under chilled conditions, preferably −5 to 5° C., most preferably at 0° C. which can be conveniently accomplished by use of an ice bath. Mechanical agitation can be rendered by use of a shaker table, vortexer, stir bar, sonication or other suitable agitation means.

In exemplary embodiments, a multi-node stir plate is used to process several samples at once. Contacting with the hydroxide salt is performed for at least 10 minutes more preferably 15-30 minutes depending on the feedstock volume and particle size. In exemplary embodiments, the time for contact with potassium hydroxide was 20 minutes.

After treatment of the feedstock with the hydroxide salt, the pH of the sample containing the feedstock and hydroxide salt is adjusted to a range suitable for the enzymatic activity of the amyloglucosidase and α-amylase using a buffer. One suitable cocktail of enzymes containing amyloglucosidase and α-amylase is commercially available from Magazyme Inc. (Chicago, IL) under the trade name MEGAZYME®. In exemplary embodiments using MEGAZYME®, the pH was adjusted by adding four volumes of sodium acetate buffer pH 4.5 to one volume of the feedstock sample containing 2 M potassium hydroxide. The enzyme cocktail containing amyloglucosidase and α-amylase is added to the pH adjusted sample and incubated at temperature and for a time sufficient to enzymatically hydrolyze almost all of the starch in the sample. The amount of enzyme cocktail to add is dependent on the activity of the enzyme expressed in units and the dry weight of the feedstock in the sample. In exemplary embodiments using MEGAZYME®, the amount of the enzyme cocktail added was to bring the sample to 3 units of each of amyloglucosidase and α-amylase per mg of dry weight of sample. One unit of amyloglucosidase activity is defined as the amount of enzyme required to release one μmole of D-glucose reducing-sugar equivalents per minute from soluble starch at pH 4.5 and 40° C. One unit of α-amylase is the amount of enzyme required to release one μmole of p-nitrophenol from blocked p-nitrophenyl-maltoheptaoside per minute (in the presence of excess α-glucosidase) at pH 6.0 and 40° C.

This sample is incubated at a sufficient temperature and time to hydrolyze least 90% of the starch to glucose forming a first soluble material fraction. In preferred practices at least 95% or at least 98% of the starch is hydrolyzed. In exemplary embodiments using MEGAZYME®, the temperature was 50° C. for and the time was 45 minutes with mechanical agitation using a shaker bath or water bath with a multi-node stir plate, which conditions were sufficient to digest 93.5% to 98.6% of the starch in the sample. The insoluble solids in the sample are separated by centrifugation and the supernatant, which is a first soluble material sample, is analyzed by HPLC to determine the amount of glucose in the sample, representing the total amount of glucose released from the starch components of the feedstock.

The insoluble material is retained for further treatment by high severity acid hydrolysis (HSAH) to determine the amount of glucose that is liberated from the remaining cellulosic components of the feedstock. Prior to subjecting the retained solids to HSAH, the retained solids should be washed with water or other suitable solvent to remove any residual soluble glucose that may remain in the sample. Preferably, the wash is repeated at least three times with at least 10 times the weight of wash fluid relative to the retained sample weight with removal of the supernatant between washes if the washing includes centrifugation to separate the solids from the wash. If filtration is used, each wash should again be at least 10 times the weight of the retained solids.

If the feedstock contains yeast, such as may be the case when the feedstock to be analyzed is a corn mash used from a fermentation to make ethanol, an error may arise from the subsequent HSAH to be performed because the yeast cells will contain endogenous β-glucan present in the yeast cell wall that will add to the total amount β-glucans measured in the sample. It has been determined that HSAH treatment of yeast cells alone liberates glucans that account for between 13.7% and 17.6% of the dry weight of yeast cells.

Figure 4:
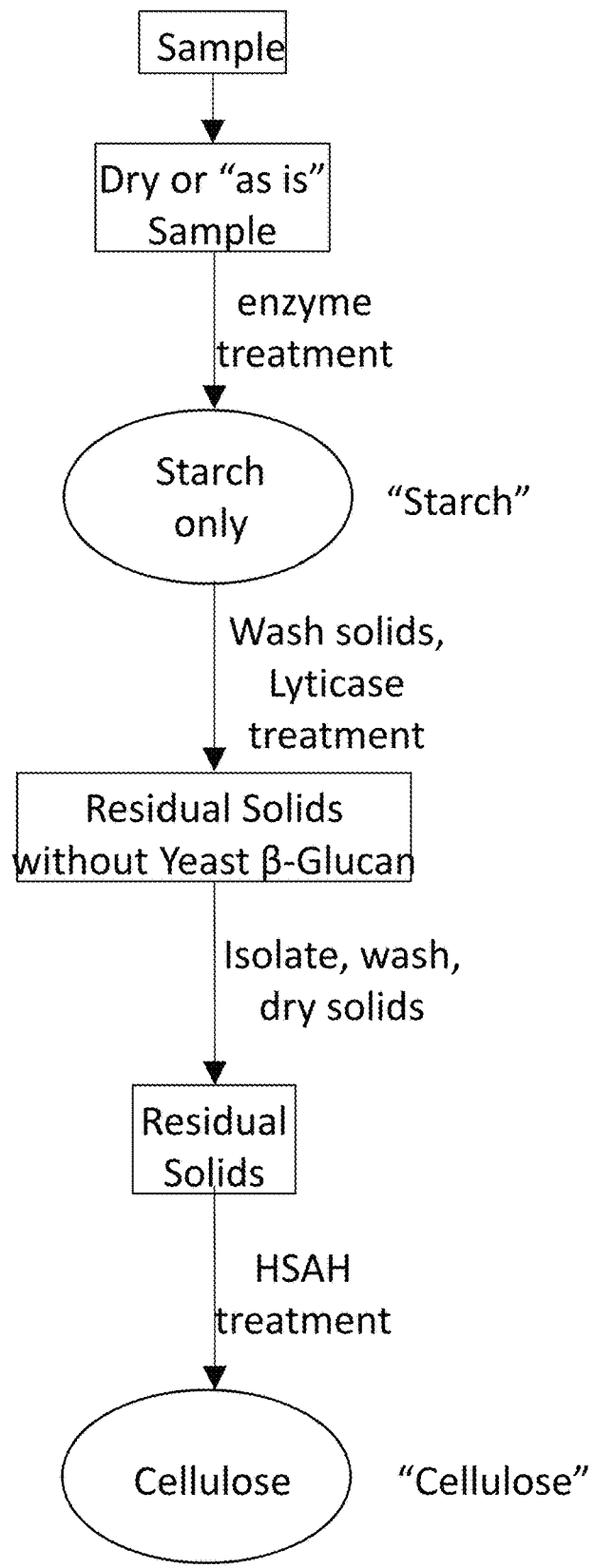
FIG. 4 is a flowchart illustrating the SEHSAH method with the optional lyticase treatment when samples contain yeast.

To overcome this problem, the retained solids fraction from the enzyme-treated feedstock that contain yeast, may optionally be contacted with lyticase to digest glucans in the cell wall prior to very severe acid hydrolysis of the solids. Lyticase is an enzyme that hydrolyzes (1,3)-β-glucans and (1,6)-β-glucans present in yeast cell walls. The process is summarized in the flowchart in FIG. 4.

One lyticase source suitable for this step is commercially available from Sigma-Aldrich (St. Louis, MO). The retained solids fraction from the enzymatic treatment step is incubated with an amount lyticase at a temperature and for a time sufficient to release at least 90% or preferably at least 95% and more preferably at least 98% of the glucans present in the yeast cell. The temperature will depend on the recommendations of the enzyme manufacture as optimal for the lyticase activity. The amount of lyticase and the time will depend on the activity of the lyticase and dry weight of the retained solids to be analyzed. In an exemplary embodiment, the amount of lyticase used was 0.5 units per mg of dry weight of the sample. One unit will produce a change in absorbance at 800 nm of 0.001/min at a pH of 7.5 and temperature of 25° C. using a suspension of yeast as substrate in a 3 mL reaction mixture. In one example, the lyticase was incubated with the sample 45-55° C. in a water bath with agitation overnight (16-24 h).

The lyticase-treated solids are washed with water at least three times to remove soluble material and the insoluble material is retained for the HSAH treatment. In a best practice, at least the first wash should be analyzed for the presence of cellobiose and/or oligomeric sugars the presence of which will indicate incomplete digestion of the yeast cell wall. In an exemplary practice where 4 ml of water was used to wash about 100 mg of lyticase-treated solids, the presence of 3 mg/ml cellobiose would be indicative of incomplete digestion, indicating the need to repeat the lyticase treatment with more lyticase, longer time or both.

Although the lyticase treatment procedure is described in the context of the SEHSAH method described in this section, lyticase treatment may also be optionally adapted for use in the previously described VSAH and SISAH methods, where the lyticase treatment procedure may be performed at any step where the yeast cells may interfere with subsequent analysis of glucose released from the starch and/or cellulosic components of a sample containing the feedstock.

The final procedure for SEHAH is the same HSAH treatment previously described above to release from β-glucans, i.e., from the cellulosic components of the feedstock. In exemplary embodiments, at least 90%, at least 95% or at least 98% of the glucose present in the cellulosic components are released into a second soluble material fraction. After separation of the solids from the second soluble fraction, the second soluble material fraction is analyzed for glucose content, preferably by HPLC which is the measure of the glucose released from the cellulosic fraction of the feedstock.

Figure 5:
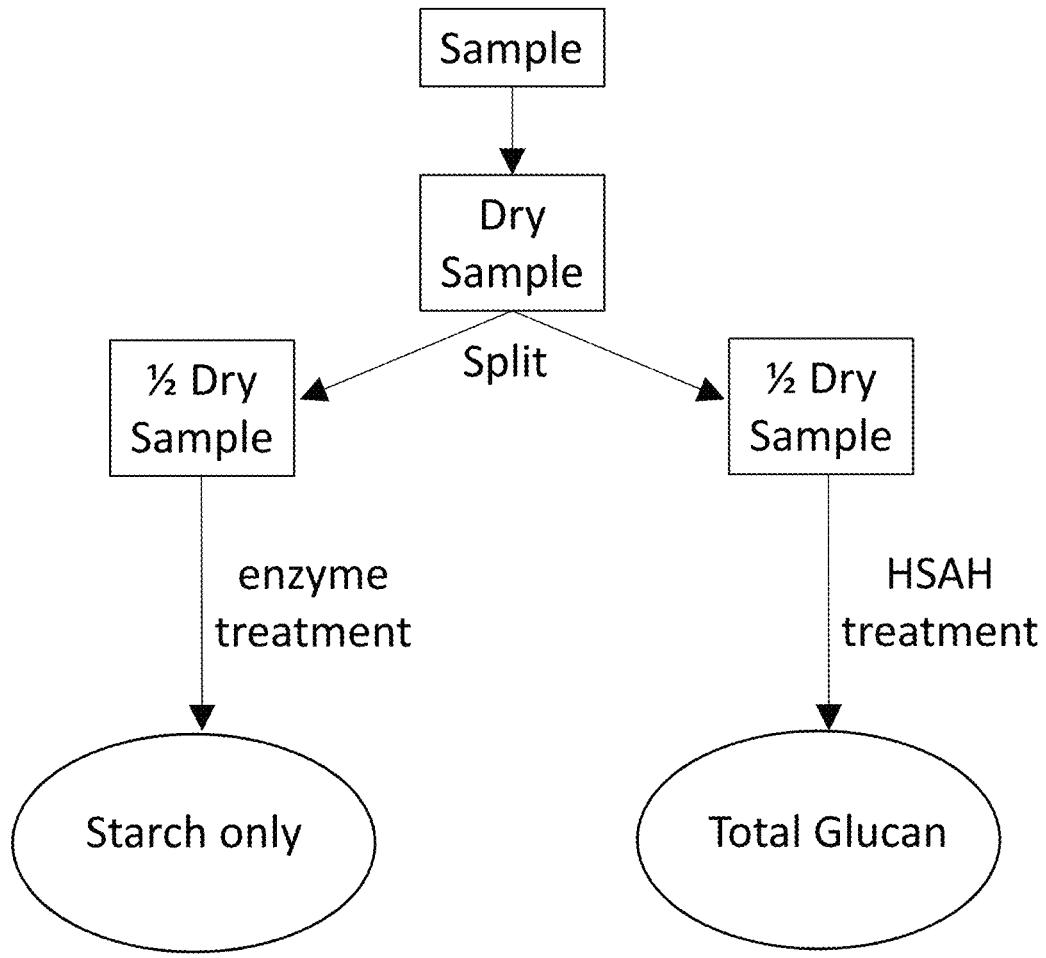
FIG. 5 is a flowchart illustrating the EHSAH method

Another embodiment of the hybrid method is parallel enzyme hydrolysis severe acid hydrolysis (EHSAH). The process is summarized in the flowchart in FIG. 5. This method is performed similar to the VSAH method, wherein the sample to be analyzed is split into two portions where one portion is subject to enzymatic digestion of starch as described above and the other portion is subject to HSAH. The amount of glucose liberated from the HSAH procedure determines the total amount of glucan obtainable from the sample. The amount of glucose measured from the enzyme treated sample is a determination of how much of the total glucan is obtained from the starch component of the sample. The amount of glucose liberated from the cellulosic component of the sample is the total amount of glucan minus the starch released glucan.

VI. Sample Pretreatment

In some embodiments, no pretreatment of the feedstock is required prior to use of the described compositions and methods. However, feedstocks used for fuel ethanol production are variable in quality and purity and may require pretreatment to maximize the accuracy and reproducibility of the assay.

Extraction using an organic solvent to remove contaminants that could interfere with the assay is a preferred method for sample pretreatment. Alcohols are well-suited extractants. While ethanol is particularly attractive for use as a solvent, as it is itself a product of an ethanol facility, suboptimal pretreatment results are obtained using ethanol alone. Superior treatment is obtained using isopropyl alcohol. Higher alcohols are also likely to be acceptable but may increase the cost and inconvenience of waste disposal.

Drying samples prior to or following extraction may also be desirable to remove traces of the extraction solvent. Drying may be performed prior to sulfuric acid treatment to control the moisture content in the hydrolysis reaction.

VII. Use of the Present Assays

The present compositions and methods are primarily for the purpose of distinguishing glucose obtainable from the cellulosic component of a feedstock from the starch component. This distinction is essential for accurately determining the amount of ethanol produced by a fuel ethanol facility that qualifies for D3 RIN credits, as opposed to, e.g., D6 RIN credits.

Nonetheless, the present compositions and methods have broader applications than the determination of D3 RINS. The present compositions and methods also represent a way to selectively hydrolyze starch to glucose in a substrate (not necessarily a feedstock) also containing cellulose. Previously, the hydrolysis of significant amounts of starch was an inevitable consequence of hydrolyzing cellulose, complicating analysis. The use of the described MSAH conditions solve this problem by selectively hydrolyzing starch at the substantial exclusion of cellulose.

The present compositions and methods can also be used to examine the residual components present in distiller's dried grains and other by-products and intermediates produced by ethanol production facilities.

VIII. Kits of Parts

The present compositions include kits of parts or "test kits" for measuring the amount of cellulose-derivable glucose in a feedstock comprising a mixture of starch and cellulosic components. Exemplary components are (i) autoclavable sample tubes, (ii) a solution of sulfuric acid at a concentration such that, when added to a sample of feedstock (or first portion of feedstock, depending on the method) at a predetermined volume ratio is sufficient to produce a first portion of the feedstock having about 30-55 wt %, or about 36-45 wt % sulfuric acid and (iii) a solution of sulfuric acid at a concentration such that, when added to a sample of feedstock (or second portion of feedstock, depending on the method) at a predetermined volume ratio is sufficient to produce a second portion of the feedstock having 63-83 wt % (and in some cases 72 wt %) sulfuric acid (iv) amyloglucosidase, α-amylase and/or lyticase enzymes and (iv) instructions for use. The kit of parts may also include a column for high performance liquid chromatography. An exemplary column is described, below.

These and other aspects and embodiments of the present compositions and methods will be apparent to the skilled person in view of the present description. The following examples are intended to further illustrate, but not limit, the compositions and methods.

EXAMPLES

Example 1. Sample Pretreatment

Feedstock samples can contain contaminating elements that could interfere with the accuracy of measurements. For instance, corn grain feedstock samples can contain significant amounts of oil that may interfere with the quantitation of starch and cellulose. To reduce this interference, the samples are dried and repeatedly washed with IPA to remove contaminating elements.

To prepare samples using the IPA-based washing method, feedstock samples of interest were thawed and homogenized. At least 10 g of wet sample was weighed and dried overnight in a vacuum oven at 75° C. The total dry solids (TDS) measurement of the samples, a calculated value consisting of the dried sample mass divided by the wet sample mass expressed as a percentage, were determined.

Dried samples were transferred to appropriate grinding vessels and ground until homogenous, then separated to replicates. An initial extraction step was completed by addition of a 1:1 volume ratio of IPA to dry sample. Masses of the initial dry sample replicates and the samples with added IPA extract volume were collected.

Extractions were incubated at ambient temperature for 30 minutes with agitation at 200 rpm. Post-extraction tubes were centrifuged at 1370 RCF for 5 minutes to pellet the solids. The supernatant was analyzed for sugar content to ensure that no sugars were removed by the IPA. Four additional IPA washes were performed on the samples in which about 10 sample volumes of IPA were added to the tube, vortexed to suspend the pellet, then centrifuged again and the supernatant discarded. The wash liquor appeared progressively lighter in color during this process.

Post-wash pellets were dried at 75° C. overnight after which the dried pellet mass values were collected and used in conjunction with the measurements collected above to calculate insoluble solids values. Before continuing to the assay, it was necessary to combine and homogenize replicate samples to gather sufficient material. This step can easily be avoided by starting with larger amounts of sample.

Example 2. Variable Severity Acid Hydrolysis (VSAH)

The VSAH method is used for measuring the converted fraction of starch and cellulose in a sample. About 30 mg of each samples of interest from Example 1 (along with the reference materials described in Example 3-5) were added into glass pressure tubes in replicate for each condition to be tested. Medium severity acid hydrolysis (MSAH) measures the starch fraction and was achieved by addition of a 44.7 wt % sulfuric acid (final concentration). High severity acid hydrolysis (HSAH) measures the total glucan (cellulose and starch) fraction and was achieved by addition of 72 wt % sulfuric acid (final concentration). The tubes were incubated at 30° C. for 1 h with agitation and stirring to ensure even contact of acid with sample.

Post-incubation, VSAH samples were diluted to a final sulfuric acid concentration of 2 wt % (MSAH) and 4 wt % (HSAH). A set of sugar recovery standards (SRS) were run in parallel with experimental samples to monitor the recovery of glucose, xylose and arabinose after autoclave processing. An aliquot of un-cooked sample was reserved for each SRS prepared and compared with the post-autoclave sample to create a recovery percentage value. Three concentrations of the SRS at both medium and high severity were analyzed (see Table 1) and the experimental samples were ultimately corrected for the recovery percentage measured.

TABLE 1

Treatment of SRS

| SRS number | MilliQ water (µl) | Sulfuric acid at 72% (µl) | Sugar standard stock (µl) |
|---|---|---|---|
| 1 | 7350 | 150 | 800 |
| 2 | 7750 | 150 | 400 |
| 3 | 7950 | 150 | 200 |
| 4 | 7200 | 300 | 800 |
| 5 | 7600 | 300 | 400 |
| 6 | 7800 | 300 | 200 |

The dilute acid containing samples were autoclaved for 45 min at 121° C. before being removed to cool to ambient temperature. Tubes were inverted to mix, then an aliquot removed from each sample. The neutralizing agent, calcium carbonate, was added as a dry powder to samples for pH adjustment and to reduce the sulfate content. The neutralization step was similarly performed on all SRS samples. Mixed and filtered samples were analyzed for glucose by HPLC using an organic acids column. A high purity glucose standard was included along with the un-hydrolyzed and hydrolyzed SRS standards in the HPLC analysis.

Example 3. Reference Sample Materials

Figure 6:
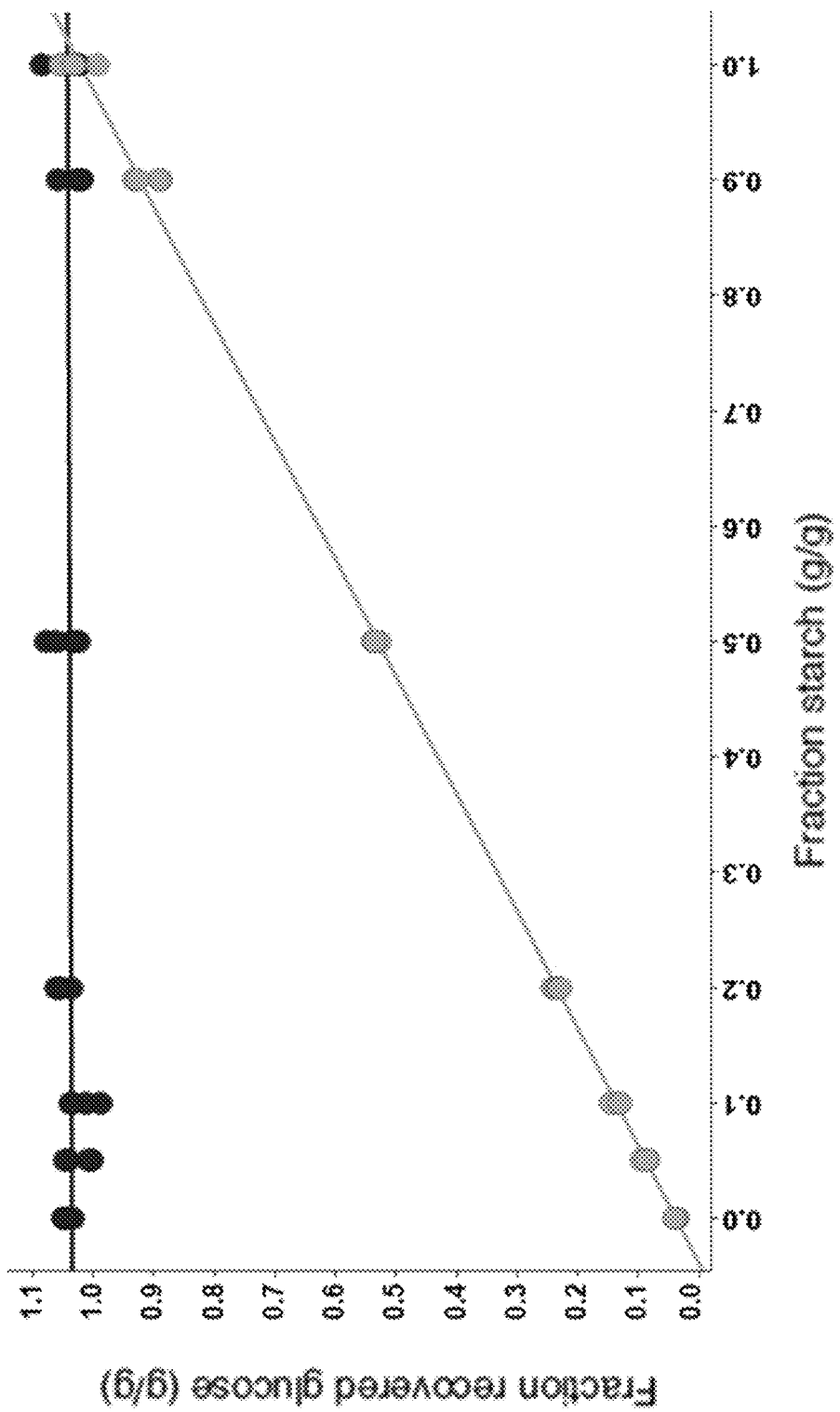
FIG. 6 is a graph showing the fraction of recovered glucose (g/g) following VSAH compared to the fraction of starch in samples having defined corn starch:Avicel ratios and treated under MSAH (grey markers) or HSAH (black markers) conditions.

A set of corn starch and Avicel (purified cellulose material; Fluka, Cat. No. 11365) blends were created. Corn starch (CS) and Avicel (A) were dried separately overnight in an oven at 75° C. The two materials were then combined in the following percent (w/w) ratios: 100:0 A:CS, 95:5 A:CS, 90:10 A:CS, 80:20 A:CS, 50:50 A:CS, 10:90 A:CS, and 0:100 A:CS. This set of reference materials was processed through the VSAH method described in Example 2. As shown in FIG. 6 and Table 2, the fraction of recovered glucose from the medium severity condition (gray circles) is directly dependent on the fraction of starch included in the reference materials. The fraction of glucose recovered from the high severity condition (black circles) is 100% for all samples. Thus, cellulosic glucan content can be calculated by subtracting the value of MSAH recovered glucose from the value of HSAH recovered glucose.

TABLE 2

Glucose recovered from corn starch and Avicel ratio reference materials

| Sample | Severity | Fraction recovered glucose (g/g) |
|---|---|---|
| 100% starch | Medium | 1.033 ± 0.029 |
|  | High | 1.046 ± 0.028 |
| 90% starch:10% Avicel | Medium | 0.910 ± 0.023 |
|  | High | 1.032 ± 0.017 |
| 50% starch:50% Avicel | Medium | 0.534 ± 0.005 |
|  | High | 1.050 ± 0.024 |
| 20% starch:80% Avicel | Medium | 0.235 ± 0.005 |
|  | High | 1.053 ± 0.012 |
| 10% starch:90% Avicel | Medium | 0.137 ± 0.006 |
|  | High | 1.019 ± 0.023 |
| 5% starch:95% Avicel | Medium | 0.088 ± 0.004 |
|  | High | 1.025 ± 0.022 |
| 100% Avicel | Medium | 0.037 ± 0.002 |
|  | High | 1.045 ± 0.008 |

Example 4. Resistant Starch Reference Materials

Starch samples with high resistant starch (RS) content were obtained from Megazyme. Potato starch (63.4% w/w RS) and a Megazyme resistant starch control (44% w/w RS) were selected for having the high resistant starch content. These reference materials were run through the VSAH method from Example 2 in parallel with the corn starch and Avicel reference materials described in Example 3. The results are summarized in Table 3. Full recovery of glucose was obtained from all samples treated with high severity (HSAH). No glucose was recovered from the cellulose sample (Avicel) treated at medium severity (MSAH), while full glucose recovery was observed for all starch samples, regardless of the resistant starch content. The results demonstrate that the VSAH assay does not incorrectly measure resistant starch as cellulose.

TABLE 3

Glucose recovered from corn starch, Avicel and resistant starch reference materials

| Sample | Severity | Fraction recovered glucose (g/g) |
|---|---|---|
| Avicel | Medium | 0.030 ± 0.003 |
|  | High | 0.959 ± 0.005 |
| Corn starch | Medium | 0.961 ± 0.005 |
|  | High | 0.967 ± 0.022 |
| Potato Starch | Medium | 1.001 ± 0.014 |
|  | High | 1.023 ± 0.007 |
| RS control | Medium | 1.005 ± 0.020 |
|  | High | 1.016 ± 0.017 |

Example 5. Additional MSAH Reference Materials

Additional reference materials containing 100% corn starch and 50:50 corn starch:Avicel were prepared as in Example 3. These reference materials were processed in the VSAH method as in Example 2, with the exception that the medium severity acid conditions were prepared to concentrations of sulfuric acid as listed in Table 4. Substantially the same glucose recovery was observed from starch samples treated with various medium concentrations of sulfuric acid and from starch and cellulose (Avicel) samples treated with various medium concentrations of sulfuric acid, all in proportion to the starch content of the sample.

TABLE 4

Glucose recovered from additional MSAH reference materials

| Incubation | Autoclave | Glucose recovered (g/g) | |
|---|---|---|---|
| $H_2SO_4$ (wt %) | $H_2SO_4$ (wt %) | 100% Starch | 50% starch:50% cellulose |
| 32.4 | 1.4 | 1.064 ± 0.008 | 0.573 ± 0.007 |
| 44.7 | 2.1 | 1.096 ± 0.009 | 0.538 ± 0.007 |
| 55.1 | 2.8 | 1.083 ± 0.009 | 0.547 ± 0.006 |

Example 6. Variation of MSAH Conditions

Additional reference materials containing 100% corn starch, 50:50 corn starch:Avicel and 100% Avicel were prepared as in Example 3. These reference materials were processed in the VSAH method as in Example 2, with the exception that one set of medium severity reference materials were not subjected to the 1 h incubation period at 30° C. Instead, this set was suspended directly in 2% sulfuric acid and autoclaved as in Example 2. Glucose recovery is summarized in Table 5. Substantially the same glucose recovery was observed from starch samples, or starch plus cellulose samples, with or without the 30° C.-incubation for 1 hour, all in proportion to the starch content of the mixtures. Essentially no glucose was recovered from cellulose with or without the 30° C. incubation for 1 hour.

TABLE 5

Glucose recovered from further additional MSAH reference materials

| | Glucose recovered (g/g) | | |
|---|---|---|---|
| Treatment | 100% starch | 50% starch:50% Avicel | 100% Avicel |
| Incubated | 1.033 ± 0.029 | 0.534 ± 0.005 | 0.037 ± 0.002 |
| Not incubated | 1.063 ± 0.061 | 0.527 ± 0.008 | 0.028 ± 0.001 |

Example 7. Serial Increasing Severity Acid Hydrolysis (SISAH)

Introduction

Samples used for this method were dried and homogenized. 30.0±3.0 mg of dried sample were weighed into a hydrolysis tube and their mass recorded. In addition to the experimental samples, 15.0±2.0 mg of control samples composed of pure starch and cellulose (Avicel) were weighed into hydrolysis tubes and their mass recorded.

MSAH Treatment

A 44.7% w/w (36% v/v) solution of sulfuric acid was prepared and 300 µL was added to each hydrolysis tube. Upon addition of the sulfuric acid, the samples were immediately stirred. The tubes were placed in a shaking incubator set at 30° C., 160 rpm agitation for 60 min. MSAH batch SRS tubes were prepared as in Table 6. The SRS stock solutions were added to the tubes last after water and acid were combined and mixed to avoid sugar damage.

TABLE 6

Preparation of MSAH batch SRS tubes

| SRS tube number | MilliQ water (µL) | 44.7% w/w sulfuric acid (µL) | SRS G/X/A stock (µL) |
|---|---|---|---|
| 1 | 7200 | 300 | 800 |
| 2 | 7600 | 300 | 400 |
| 3 | 7800 | 300 | 200 |

After thorough mixing, 1 mL of each SRS sample was removed and placed in a separate glass borosilicate tube as a pre-hydrolysis sample. Following 60 min incubation, the tubes were removed from the shaking incubator and 8 mL MilliQ water was added to each hydrolysis tube to dilute to 2% w/w sulfuric acid. The samples were mixed thoroughly and autoclaved for 45 min at 121° C. followed by centrifugation at 1370 RCF for 10 min. 1 mL of supernatant was removed from each tube and transferred to a glass borosilicate tube. Supernatants were neutralized by addition of approximately 35 mg calcium carbonate.

200 µL neutralized samples were filtered through a 0.22-µM filter plate and analyzed by HPLC. The remaining supernatant was removed from the centrifuged hydrolysis tubes containing samples using a vacuum siphon. 5 mL MilliQ water was added to residual pellets followed by vortexing to re-suspend solids. The tubes were centrifuged at 1370 RCF for 5 min and the wash steps with water were repeated two additional times. The tubes were then placed upright in a rack at 65° C. in a conventional drying oven for 16-24 h.

HSAH Treatment

Dried residual samples in hydrolysis tubes were removed from the oven. The tubes were placed in an ice bath and 60 µL chilled MilliQ water was added to each tube to suspended solids. 90 µL of 98% w/w chilled sulfuric acid was added to each hydrolysis tube followed by immediate mixing. The tubes were placed in a shaking incubator set at 30° C. with 160 RPM agitation for 60 min. HSAH batch SRS tubes were prepared as summarized in Table 7. As before, the SRS stock solutions were added to the tubes last after water and acid were combined and mixed to avoid sugar damage.

TABLE 7

Preparation of HSAH batch SRS tubes

| SRS tube number | MilliQ water (µL) | 98% w/w sulfuric acid (µL) | SRS G/X/A stock (µL) |
|---|---|---|---|
| 4 | 3660 | 90 | 400 |
| 5 | 3860 | 90 | 200 |
| 6 | 3960 | 90 | 100 |

After thorough mixing, 1 mL of each SRS was removed into a separate glass borosilicate tube as a pre-hydrolysis sample. Following 60 min incubation, the tubes were removed from the shaking incubator and 4 mL MilliQ water was added to each hydrolysis tube to dilute to 4% w/w sulfuric acid. The contents of the hydrolysis tubes were mixed thoroughly and autoclaved for 45 min at 121° C. A 1 mL aliquot of supernatant was removed from each hydrolysis and SRS tube and transferred to a glass borosilicate tube. Supernatants were neutralized by addition of approximately 70 mg calcium carbonate. 200 uL neutralized samples were filtered through a 0.22-micron filter plate and analyzed by HPLC.

Results

As shown in Table 8, under the medium severity conditions (MSAH), the Avicel PH-101 (Fluka, Cat. No. 11365) sample releases almost no glucose but releases all glucose in the subsequent high severity conditions (HSAH). The starch (Sigma Aldrich, Cat. No. S4180) sample releases all glucose under the medium severity condition with no glucose released in the subsequent high severity condition. Biomass sample A is a starch-rich sample from the beginning of a corn grain ethanol process and releases a high level of glucose in the medium severity condition and a low level of glucose in the high severity condition. Biomass B is a starch-depleted sample from the end of the corn grain ethanol process and releases a low level of glucose from both the medium severity and the subsequent high severity conditions.

The observation that 3.2% glucose is released in MSAH treatment of Avicel may be the result of minor cellulose solubility in the MSAH condition. Avicel is created from plant-based materials and is primarily composed of cellulose, but will contain residual amounts of xyloglucan, β-glucan or other glucose-containing polymers typically present in plant material.

TABLE 8

Glucose recovered from starch and cellulose containing samples

| Sample | Conditions | Fraction recovered glucose (g/g) |
|---|---|---|
| 100% Avicel | MSAH | 0.032 ± 0.011 |
| | HSAH | 0.962 ± 0.021 |
| 100% starch | MSAH | 1.004 ± 0.036 |
| | HSAH | 0.000 ± 0.000 |
| Biomass A | MSAH | 0.663 ± 0.051 |
| | HSAH | 0.012 ± 0.001 |
| Biomass B | MSAH | 0.066 ± 0.001 |
| | HSAH | 0.046 ± 0.004 |

Example 8. VSAH Using Fermentation Biomass

Samples of corn starch, resistant starch, Avicel, Bagasse, dextrose, and biomass from an ethanol fermentation mash are included in this example. Two types of biomasses were analyzed: (i) pre-post-conversion fermentation slurries containing a liquefied corn mash and (ii) post-fermentation slurries, which included yeast cells. To perform the VSAH step, these samples were split for parallel treatments with either MSAH to determine the total non-cellulosic glucans released by medium severity acid hydrolysis or HSAH to determine the total glucans present in the sample which would be released by high severity acid hydrolysis of both the starch and cellulosic components, as well as any glucans released from yeast present in the post-fermentation biomass.

The biomass samples were initially dried and washed with IPA as described in Example 1. To ensure homogeneity, the samples were ground mechanically to reduce particle size prior to analysis. About 30 mg of each sample was added into headspace vials in replicate for each condition to be tested. 36 wt % sulfuric acid (final concentration) was added for the VSAH samples subjected to MSAH. 72% sulfuric acids (final concentration) was added for the VSAH samples subjected to HSAH. The vials were incubated at 30° C. with 150-200 rpm agitation to ensure even contact of acid with sample for 60 min.

Post-incubation, VSAH samples were diluted to a final sulfuric acid concentration of 2 wt % for MSAH and 4 wt % for HSAH treatment. A set of sugar recovery standards (SRS, 2 g/L dextrose solution) were run in parallel with the control and experimental samples to monitor the recovery of glucose after autoclave processing. An aliquot of un-cooked sample was reserved for each SRS prepared and compared with the post-autoclave sample to create a recovery percentage value. The experimental samples were ultimately corrected for the recovery percentage measured.

The dilute acid-containing samples were autoclaved for 60 min at 120° C. before being removed to cool to ambient temperature. Tubes were inverted to mix, then an aliquot removed from each sample. Mixed and filtered samples were analyzed for glucose by HPLC using a Biorad 87H. A high purity glucose standard was included along with the un-hydrolyzed and hydrolyzed SRS standards in the HPLC analysis. Equivalent results on the Biorad 87H were obtained when analyzing post-hydrolysis samples "as-is" and upon addition of the neutralizing agent, calcium carbonate.

Non-cellulosic glucan was determined by measuring the glucose liberated upon MSAH. The term "non-cellulosic glucan" is used in this example because the mid-severity acid hydrolysis conditions were shown to hydrolyze not only the total starch but also hemicellulose, and 1,3-β-glucans and 1,6-β-glucans from yeast cell walls. Total glucan was determined by measuring the total number glucans released under parallel HSAH conditions. In this method the total glucans attributed to, cellulose is determined by difference through Equation 1.

[Total glucan measured by HSAH]−[Non-cellulosic glucan measured by MSAH]=[Cellulose glucan]   Equation 1:

Results

SRS samples were also prepared as described in Example 7 and analyzed for glucose recovery. Glucose (i.e., dextrose) recovered was excellent, exceeding 98% (Table 9) indicating the hydrolysis conditions did not substantially cause degradation of glucose. The controls using commercially available materials were run in duplicate to ensure that MSAH conditions did not hydrolyze cellulose and that accurate recoveries were achievable. In all cases where hydrolysis was expected, greater than 93% of known glucose available was recovered. Avicel PH-101 (Manufacturer: Fluka, PN: 11365) and Sugarcane Bagasse Whole Biomass Feedstock (Manufacturer: NIST, PN: 8491) standards do not contain starch, but do contain low levels of hemicellulose which would yield a small amount of glucose hydrolysis, as was demonstrated. The results with these standards were reliably precise having a relative standard deviation percentage (RSD) between 0.5 and 5.5% of the average value (Table 10).

Biomass samples were tested using fermentation broths after liquefaction (pre-conversion biomass samples A1-A3) and after fermentation was complete (post-conversion biomass samples B1-B3). Samples were collected from a batch fermentation process where each sample represents a different batch from the same facility. Each sample was run in quadruplicate with no outliers removed. Pre-conversion results for glucose derived from non cellulose glucan again showed high precision with an RSD of between 1.1% and 6.9%. This small variability in starch error, however, greatly impacts the cellulose result when determined using the difference method according to Eqn 1 because the amount of glucose from starchy material is roughly 10 to 20 times the amount present in cellulosic material. As a result, the calculated glucose derived from cellulose materials have larger batch-to-batch variability (13-34% RSD for pre-conversion cellulose) than for post-conversion cellulose (9% to 20%) (Table 11).

TABLE 9

SRS Recovery

| SRS number | Initial glucose (g/kg) | Final glucose (g/kg) | Glucose recovery (%) |
|---|---|---|---|
| 1 | 1.9226 | 1.8887 | 0.98 |
| 2 | 1.9603 | 1.9359 | 0.99 |
| 3 | 1.8606 | 1.8686 | 1.00 |
| 4 | 1.9133 | 1.9133 | 0.99 |

TABLE 10

VSAH results using controls

| Standard Material | MSAH Recovery (%) | % RSD | HSAH Recovery (%) | % RSD |
|---|---|---|---|---|
| Corn Starch | 98.1 | 0.28 | 93.8 | 5.35 |
| Resistant Starch | 97.9 | 0.77 | 96.5 | 0.54 |
| Avicel | 2.3 | 8.22 | 97.6 | 0.89 |
| Bagasse | 7.9 | 8.59 | 95.7 | 1.08 |
| Dextrose | 99.3 | 0.98 | 98.7 | 1.04 |

TABLE 11

VSAH results using biomass

| Sample ID | Non-cellulosic glucan (g/kg) | Relative standard deviation (%) | Cellulose (g/kg) | Relative standard deviation (%) |
|---|---|---|---|---|
| Biomass A1 | 605 | 1.09 | 32.2 | 24.2 |
| Biomass A2 | 621 | 1.56 | 15.5 | 33.9 |
| Biomass A3 | 545 | 6.86 | 70.9 | 12.5 |
| Biomass B1 | 78.3 | 2.85 | 57.4 | 19.8 |
| Biomass B2 | 82.2 | 14.7 | 65.2 | 10.1 |
| Biomass B3 | 66.3 | 8.05 | 71.2 | 8.93 |

Example 9. HSAH Condition Range

The exemplified HSAH conditions were routinely 72% sulfuric acid. To determine whether a broader range of sulfuric acid concentration would be suitable, a range of sulfuric acid concentrations were tested and compared to the standard of 72% for samples of corn starch and corn fiber. A screening test with high starch/corn fiber biomass material demonstrated the range of high severity acid concentration suitable for HSAH was 63-83% sulfuric in terms liberating equivalent glucan. (Table 12). It should be noted, however, that sulfuric acid concentrations above 78% become challenging because of viscosity and are not recommended.

TABLE 12

Sulfuric acid ranges

| Sulfuric acid concentration, wt % | Cellulosic glucan, wt % (dry basis) | Difference from 72%, wt % |
|---|---|---|
| 60 | 2.31 | −0.27 |
| 60 | 2.27 | −0.31 |
| 63 | 2.58 | 0 |
| 63 | 2.57 | −0.01 |
| 67 | 2.59 | 0.01 |
| 67 | 2.56 | −0.02 |
| 70 | 2.50 | −0.08 |
| 70 | 2.60 | 0.02 |
| 72 | 2.58 | — |
| 78 | 2.46 | −0.12 |
| 81 | 2.47 | −0.11 |
| 83 | 2.44 | −0.14 |

Sulfuric acid concentrations of about 63-83% provide similar results.

Example 10. Hydrolysis of β-Glucans in Yeast Cell Mass Under by VSAH Treatment

A potential interference in determination of "cellulosic content", which is defined by the US EPA specifically as cellulose, hemicellulose, or lignin, is β-glucan contribution from yeast cell mass that is accumulated during in situ fermentation. In this example, VSAH conditions were tested on yeast alone to evaluate the effects on acid hydrolysis of yeast glucans.

Active dry ETHANOL RED® yeast from Lesaffre (1 g), commonly used in the U.S. ethanol production industry, was hydrated with water at room temperature for 15 minutes. The hydrated cells were pelleted, and the solid pellet was washed 3 times with isopropyl alcohol. The solids were dried at 75° C. overnight. Dried, washed solids were ground using an appropriate milling device. VSAH was performed on the dried yeast as described in Example 8 (i.e, using (MSAH and HSAH in a parallel method).

Results

Glucan from yeast cells was in fact released by hydrolysis under both MSAH and HSAH conditions, with varying precision in experimental results between the MSAH and HSAH treatments. The degree of variation in experimental results was higher for MSAH treatment. It was determined that about 13.2-19.4% of the dry weight of the yeast was released by both MSAH and HSAH treatment. Therefore, without modification, the β-glucans released from yeast cells present in post-conversion fermentation samples would increase both the total glucans and non-cellulose glucans in Equation 1.

Example 11 Serial Increasing Severity Acid Hydrolysis (SISAH) with Fermentation Biomass As noted elsewhere, the SISAH method was developed with the intention of removing variability associated measuring a very large concentration of one analyte (starch, 62-72 wt %, dry basis) relative to a very small concentration of another analyte (cellulose, 1-4 wt %, dry basis). A 2-4% variability in measurement of the large starch component could substantially reduce the reliability of the small measurement of the cellulose component when based on determination by difference. Pre-conversion and post-conversion biomass samples from ethanol fermentation used for this method were dried and homogenized as in Example 8. 30.0±3.0 mg of dried samples were weighed into a headspace vial and their mass recorded. In addition to the experimental samples, 15.0±2.0 mg of control samples including pure corn starch (Sigma, PN S9679), microcrystalline cellulose (Sigma, PN C6413), resistant starch (Megazyme, K-RSTCL) were weighed into headspace vials and their mass recorded. SRS samples were also prepared as previously described.

MSAH Treatment

Sulfuric acid for a 36 wt % MSAH treatment was made by adding 210 µL of water followed by the addition of 90 µL of 98% sulfuric acid to each headspace vial containing the dried samples. Upon each reagent addition, the samples were immediately stirred. The vials were placed in a shaking incubator set at 30° C. with 150-200 rpm agitation for 60 min.

Following 60 min incubation, the tubes were removed from the shaking incubator and 8 mL MilliQ water was added to each hydrolysis tube to dilute to 2% w/w sulfuric acid. MSAH batch SRS tubes were prepared by dispensing 300 µl of SRS into a labeled headspace vial. Then 8 mL of water followed by 90 µL of 98% sulfuric acid was added to each headspace vial. The samples were mixed thoroughly and autoclaved for 60 min at 121° C. followed by centrifugation at 1370 RCF for 10 min. 2 mL of supernatant was removed from each tube and transferred to a glass borosilicate tube. Samples were filtered through a 0.22-micron filter and analyzed by HPLC.

Aliquots of 1 mL of water were added to the headspace vials, then quantitatively transferred into the corresponding 15 mL centrifuge tube. The headspace vial was rinsed 4 times. The tubes were centrifuged at 2930 RCF for 5 min, and supernatant carefully removed. Water (4 mL) was added to solids in centrifuge tube to wash solids, then centrifuged at 2930 RCF for 5 min, and liquor removed. The wash was repeated two more times. The tubes were then placed upright in a rack in a vacuum oven at 45±3° C. with a reduced pressure at 75±15 mmHg above complete vacuum (or −685±15 mmHg from atmospheric pressure at sea level) for 16-24 h.

HSAH Treatment

Dried residual samples in hydrolysis tubes were removed from the oven and allowed to cool. The solid pellet in each tube was manually pulverized with a disposable rod, leaving the rod in the tube as an agitation aid. HSAH treatment conditions (72 wt % sulfuric acid) were achieved by adding 60 µL of water followed by the addition of 90 µL of 98% sulfuric acid to each centrifuge tube. Upon each reagent addition, the samples were immediately stirred. Alternatively, 150 µL of 72% sulfuric acid was added to each centrifuge tube. The tubes were placed in an oven shaker set at 30° C. with 150-200 rpm agitation for 60 minutes.

Using 1 mL aliquots of water, post-incubation material was quantitatively transferred from centrifuge tubes to pre-weighed and labeled headspace vials. Water (1 mL) was added to the sample, transferred, then 3×1 mL additions were used to rinse any residue into headspace vial, totaling 4 mL of water to dilute to 4% sulfuric acid. Gross weight of vial and contents was recorded before and after autoclaving to monitor any potential material loss.

HSAH batch SRS tubes were prepared by dispensing 300 µL of SRS stock solution into labeled headspace vials. 4 mL of water was added, followed with the addition of 90 µL of 98% sulfuric acid to each SRS headspace vial. A 1 mL aliquot was taken and filtered into an HPLC vial for pre-hydrolysis analysis.

The contents of the hydrolysis headspace vials were mixed thoroughly and autoclaved for 45-60 min at 121° C. Cooled contents were optionally neutralized by addition of approximately 70 mg calcium carbonate, allowed to settle. Samples were filtered through a 0.22-micron filter and analyzed by HPLC.

Results

By analyzing samples using this SISAH method rather than the parallel analysis comprising the MSAH results to the HSAH methods, the variability of the pre-conversion cellulose concentration was reduced. Removing the impact of a small error in measurement of total starch and taking a more direct measurement of cellulose allows for reduced variability. Each of the control samples again showed high precisions with a % RSD of between 0.05 and 3.6% (Table 13). The relative standard deviation in analysis of cellulose in the same set of pre-conversion samples used in Example 8 was reduced from a highest value of 34% to a highest value of 13% (Table 14). Batch-to-batch variability was also reduced to 4.7% RSD

TABLE 13

SISAH control standard recoveries

| Standard Material | SISAH, Glucose recovery (%) | % RSD |
|---|---|---|
| Corn Starch A | 96.5 | 0.55 |
| Corn Starch B | 95.9 | 0.05 |
| Corn Starch C | 98.6 | 0.44 |
| Resistant Starch A | 95.0 | 0.49 |
| Resistant Starch B | 93.5 | 0.21 |
| Resistant Starch C | 96.1 | 0.01 |
| Cellulose A | 94.0 | 3.63 |
| Cellulose B | 91.8 | 0.93 |
| Cellulose C | 91.5 | 0.52 |

TABLE 14

SISAH results using biomass samples

| Sample ID | Non-cellulosic glucan (g/kg) | Relative standard deviation (%) | Cellulose (g/kg) | Relative standard deviation (%) |
|---|---|---|---|---|
| Biomass A1 | 606 | 0.71 | 13.5 | 12.73 |
| Biomass A2 | 618 | 0.14 | 12.3 | 12.41 |
| Biomass A3 | 601 | 0.77 | 13.3 | 4.30 |
| Biomass B1 | 69.2 | 5.57 | 42.0 | 8.57 |
| Biomass B2 | 83.0 | 7.92 | 44.8 | 6.98 |
| Biomass B3 | 76.0 | 8.75 | 47.2 | 7.72 |

Example 14. Parallel Enzymatic and Severe Acid Hydrolysis (EHSAH)

In this example, instead of using parallel MSAH and HSAH conditions as in the VSAH method, MSAH conditions are replaced with an enzymatic method that degrades only starch. This method avoids inaccuracy that may arise from the presence of yeast glucans in the sample, because the enzymes used do not digest the glucans present in the yeast cell wall.

Enzyme Treatment

Samples (1 g) were weighed into a test tube in duplicate, at minimum. In addition to the experimental biomass samples, which were liquid slurries, 100 mg of control samples of pure corn starch (Sigma, PN S9679), microcrystalline cellulose (Sigma, PN C6413), resistant starch (Megazyme, K-RSTCL) were weighed into centrifuge tubes and their mass recorded. 0.5 mL of 80% ethanol was added to the solid samples to aid in dispersion. Tubes were placed in a rack and submerged in an ice bath with mechanical stirring. 2 mL of 2 M potassium hydroxide was added to solid samples; 1 mL of 4 M potassium hydroxide was added to liquid samples and stirred in an ice bath for 20 min.

To each tube treated with hydroxide, 8 mL of 1.2 M sodium acetate buffer pH 4.5 was added to adjust pH. 0.1 mL of MEGAZYME® was added to the samples. As mentioned elsewhere, MEGAZYME® is a trade name for a commercially available enzyme cocktail that contains the starch hydrolyzing enzymes amyloglucosidase and α-amylase (Magazyme PN: E-AMGDF). The amount of enzyme added brought the dosage rate to 3 units of amyloglucosidase and 3 units of -amylase per mg sample. One unit of amyloglucosidase activity is defined as the amount of enzyme required to release one μmole of D-glucose reducing-sugar equivalents per minute from soluble starch at pH 4.5 and 40° C. One unit of α-amylase is the amount of enzyme required to release one μmole of p-nitrophenol from blocked p-nitrophenyl-maltoheptaoside per minute (in the presence of excess α-glucosidase) at pH 6.0 and 40° C. The enzyme-treated tubes were incubated for 45 min at 50° C. in a shaker bath, followed by a 10-minute enzyme deactivation step in a 95-100° C. water bath or convection oven for 10 minutes. Samples were allowed to cool for 10 min.

HSAH Treatment

Duplicates of the samples subject to the enzyme treatment were also subject to HSAH treatment. The samples were mixed thoroughly and 300 mg of sample "as is" was weighed into a 15 mL centrifuge tube. To each tube, 0.5±0.01 mL of water was added, followed with the addition of 2.5±0.01 mL of 86.4% sulfuric acid and vortexing. The tubes were placed in an oven shaker set at 30° C. at 150-200 rpm and incubate the sample for 55-65 minutes. After incubation, 84 mL of water was used to transfer contents to 100 mL pressure vessels (final concentration 4% sulfuric acid).

HSAH batch SRS tubes were prepared by dispensing 3 mL of SRS stock solution into labeled pressure vessel, followed addition of 81 mL of water, then 2.5 mL of 86.4% sulfuric acid. A 1 mL aliquot was taken and filtered into an HPLC vial for pre-hydrolysis analysis.

The contents of the hydrolysis headspace vials were mixed thoroughly and autoclaved for 45-60 min at 121° C. Samples were filtered through a 0.22-micron filter and analyzed by HPLC. This result yields the total β-glucans for use Equation 2.

[Total glucan measured by HSAH]−[Glucan released by enzymatic digestion of starch]=[Total β-glucan]  Equation 2:

Results

As shown in Table 15, a batch-to-batch variability of 1.60% RSD and 24% RSD for pre-conversion starch and cellulose was achieved, respectively.

TABLE 15

| Parallel analysis of 10 batch fermentations using enzyme and HSAH | | | | |
|---|---|---|---|---|
| Sample ID | Pre-conversion, starch (wt %) | Post-conversion starch (wt %) | Pre-conversion, β-glucan (wt %) | Post-conversion, β-glucan (wt %) |
| Biomass 1 | 61.8 | 2.86 | 1.17 | 6.08 |
| Biomass 2 | 61.2 | 2.37 | 1.52 | 5.29 |
| Biomass 3 | 62.1 | 2.87 | 1.14 | 5.22 |
| Biomass 4 | 63.0 | 3.25 | 1.19 | 5.15 |
| Biomass 5 | 63.2 | 2.54 | 1.07 | 5.52 |
| Biomass 6 | 64.6 | 2.79 | 0.81 | 5.67 |
| Biomass 7 | 63.7 | 3.27 | 0.83 | 5.59 |
| Biomass 8 | 63.0 | 2.75 | 1.60 | 5.57 |
| Biomass 9 | 63.6 | 3.02 | 1.02 | 5.69 |
| Biomass 10 | 63.4 | 2.94 | 0.89 | 5.93 |
| Average | 63.0 | 2.87 | 1.12 | 5.57 |
| % RSD | 1.60 | 9.77 | 23.89 | 5.36 |

Example 15. Serial Enzyme Hydrolysis and Severe Acid Hydrolysis (SEHSAH)

In this SEHSAH method, enzymatic digestion of starch replaces the MSAH in the SISAH method. Samples used for this method may either be dried and homogenized as in Example 1 or used directly as the liquid slurry from pre-conversion and post conversion fermentation broth as in Example 14.

Enzyme Treatment

100±10.0 mg of dried sample or 1.0 mL of liquid sample were weighed into a centrifuge tube and their mass recorded. In addition to the experimental samples, 100 mg of control samples composed of pure corn starch (Sigma, PN S9679), microcrystalline cellulose (Sigma, PN C6413), resistant starch (Megazyme, K-RSTCL) were weighed into centrifuge tubes and their mass recorded. 0.5 mL of 80% ethanol was added to the solid samples and controls to aid in dispersion. Tubes were placed in a rack and submerged in an ice bath with mechanical stirring. 2 mL of 2 M potassium hydroxide was added to solid samples; 1 mL of 4 M potassium hydroxide was added to liquid samples and stirred in an ice bath for 20 min.

The enzyme cocktail containing amyloglucosidase and α-amylase was added as described in Example 14. The enzyme-treated tubes were incubated for 45 min at 50° C. in a shaker bath, followed by a 10-minute enzyme deactivation step in a 95-100° C. water bath or convection oven for 10 minutes. Samples were allowed to cool for 10 min.

Samples were centrifuged at 2930 RCF for 5 min. A 1-2 mL aliquot of liquor was transferred to a vial and retained for HPLC analysis. 4 mL water was added to solids in centrifuge tube to wash residual solids, centrifuged at 2930 RCF for 5 min, and liquor removed. Water wash was repeated three more times. The tubes were then placed upright in a rack in a vacuum oven at 45±3° C. with a reduced pressure at 75±15 mmHg above complete vacuum (or −685±15 mmHg from atmospheric pressure at sea level) for 16-24 h.

HSAH Treatment

Dried residual samples in hydrolysis tubes were removed from the oven and allowed to cool. Sulfuric acid (72 wt %) was generated by adding 60 μL of water followed by the addition of 90 μL of 98% sulfuric acid to each centrifuge tube. Upon each reagent addition, the samples were immediately stirred. The tubes were placed in an oven shaker set at 27-33° C. at 150-200 rpm and incubate the sample for 60±5 minutes.

Using 1 mL aliquots of water, post-incubation material was quantitatively transferred from centrifuge tubes to pre-weighed and labeled headspace vials. It is suggested to add 1 mL of water to sample, transfer, then use 3×1 mL additions to rinse any residue into headspace vial, totaling 4 mL of water to dilute to 4% sulfuric acid. Gross weight of vial and contents was recorded before and after autoclaving to monitor any potential material loss.

HSAH batch SRS tubes were prepared by dispensing 300 µL of SRS stock solution into labeled headspace vials. 4 mL of water was added, followed with the addition of 90 µL of 98% sulfuric acid to each SRS headspace vial. A 1 mL aliquot was taken and filtered into an HPLC vial for pre-hydroysis analysis. The contents of the hydrolysis headspace vials were mixed thoroughly and autoclaved for 45-60 min at 121° C. Cooled contents were filtered through a 0.22-micron filter and analyzed by HPLC. Results are shown in Table 16 and Table 17.

Results

Performing the enzymatic and acid hydrolysis steps in series reduced the variability of analysis of pre-conversion cellulose concentration and batch-to-batch variability. This marginal variability will greatly increase the opportunity to measure small conversions of cellulose during in situ fermentations.

TABLE 16

SEHSAH results using biomass samples

| Sample ID | Pre-conversion cellulose, wt % (dry basis) | Post-conversion cellulose, wt % (dry basis) |
|---|---|---|
| Biomass X | 1.42 | 5.41 |
| Biomass Y | 1.35 | 5.98 |
| Biomass Z | 1.50 | 5.91 |
| Average | 1.42 | 5.76 |
| % RSD | 5.52 | 5.41 |

TABLE 17

SEHSAH pre-conversion cellulose batch variability

| Sample ID | Pre-conversion cellulose, wt % (dry basis) |
|---|---|
| Biomass X2 | 1.51 |
| Biomass Y2 | 1.56 |
| Biomass Z2 | 1.51 |
| Average | 1.53 |
| % RSD | 2.04 |
| Batch Average | 1.48 |
| Batch % RSD | 4.93 |

Example 16. SEHSAH and Removing Yeast β-Glucan Interference

β-glucan from yeast cell mass will contribute to the acid hydrolysis glucose results in the forgoing SEHSAH example as well as any method that uses severe acid hydrolysis of a sample that contains measurable amounts of yeast cells. Thus, if targeting conversion of corn fiber cellulose, a false mass balance will be generated by including the glucose released from the yeast as part of the total glucans released by severe acid hydrolysis.

In this example, to remove the glucose contribution from yeast cell mass, a secondary enzymatic hydrolysis step was performed prior to acid hydrolysis using a lyticase enzyme (Manufacturer: Sigma, PN: L-576 (1,200 Units/mg)). Lyticase is an enzyme that hydrolyzes 1,3-β-glucans and 1,6-β-glucans present in yeast cell walls. One unit will produce a change in absorbance at 800 nm of 0.001/min at a pH of 7.5 and temperature of 25° C. using a suspension of yeast as substrate in a 3 mL reaction mixture. The dosage rate used in this example was 0.5 Units/mg of sample to selectively hydrolyze 1,3-β-glucans and 1,6-β-glucans without hydrolysis of the 1,4-β-glucans that comprise cellulose.

Lyticase Hydrolysis Controls

Initial testing using cream yeast and YPD (yeast extract peptone dextrose) yeast were conducted to evaluate the glucose liberated upon high severity acid hydrolysis. A stock solution of each yeast was prepared and run in duplicate through HSAH conditions as described in the foregoing Examples. Then, a yeast cell count of post-conversion biomass samples was performed and the average expected glucose contribution from yeast cell wall hydrolysis was estimated to provide a benchmark for anticipated change from lyticase hydrolysis. The results are shown in Table 18.

TABLE 18

Glucans released from yeast samples

| Yeast Sample | Glucan, wt % (dry basis) | Glucan from yeast in post-conversion biomass, wt % (projected, dry basis) |
|---|---|---|
| YPD A | 13.69 | 1.08 |
| YPD B | 13.65 | 1.07 |
| Cream A | 16.83 | 1.33 |
| Cream B | 17.59 | 1.38 |

Biomass Lyticase Hydrolysis

A 0.2 mg/ml solution was prepared by weighing 5 mg of lyticase powder into a 25 ml volumetric flask and diluting with 100 mM potassium phosphate buffer (pH 6.5). Dried solids obtained after enzyme treatment as in Example 15 were suspended in 8 mL of 100 mM phosphate buffer (pH 6.5) in a pre-labeled centrifuge tube. To each pre-labeled centrifuge tube, 0.2 mL of prepared lyticase was added (0.48 Units/mg of sample) followed by incubation at 45-55° C. in a water bath with agitation overnight (16-24 h). The solution was centrifuged, and a 1-2 mL aliquot of liquor was retained for analysis by HPLC. The residual solids were washed with 4 mL of water, centrifuged at 2930 RCF for 5 min, liquor discarded. The wash was repeated three additional times. The residual solids now represent material free of starch and free of β-glucan contributed from yeast cell mass. HSAH treatment of the residual solids liberates glucose selectively from cellulose (1,4-β-glucan).

Experimental results showed that without treatment with lyticase, the glucan result in post-conversion biomass samples were 1-2 wt % higher than samples treated with lyticase (Table 19). This change is in line with estimated contribution based on yeast cell count and HSAH control experiments. Glucan in pre-conversion biomass samples did not change outside the error of the experiment.

TABLE 19

Post-conversion biomass samples treated
with and without lyticase before HSAH

| Sample ID | No lyticase glucan, wt % (dry basis) | Lyticase glucan, wt % (dry basis) |
|---|---|---|
| Biomass X | 5.41 | 4.44 |
| Biomass Y | 5.98 | 4.06 |
| Biomass Z | 5.91 | 4.38 |

What is claimed is:

1. A method for measuring an amount of cellulose-derivable glucose in a feedstock comprising a mixture of starch and cellulosic components, comprising:
    dividing the feedstock into a first portion and a second portion;
    contacting the first portion of the feedstock with about 30 to about 55 wt % sulfuric acid for about 1 hour, optionally at about 30° C., followed by
    diluting the first portion of the feedstock to 2 wt % sulfuric acid and continuing incubation for about 45 minutes under autoclave conditions,
    determining an amount of non-cellulose derivable glucose present in the first portion;
    contacting the second portion of the feedstock with about 63-83 wt % sulfuric acid for about 1 hour at about 30° C., followed by
    diluting the second portion of the feedstock to 4 wt % sulfuric acid and continuing incubation for about 45 minutes under autoclave conditions;
    determining an amount of total glucose in the second portion; and
    comparing the amount of non-cellulosic-derivable glucose determined in first portion with the amount of total glucose determined in the second portion to determine the amount of cellulose-derivable glucose in the feedstock, where an increased amount of glucose in the total glucose in the second portion of the feedstock contacted with 63-83 wt % sulfuric acid compared to the amount of glucose in the non-cellulose derivable glucose in the first portion of the feedstock contacted with about 30 to about 55 wt % sulfuric acid corresponds to cellulose-derivable glucose in the feedstock.

2. The method of claim 1, wherein the first portion of the feedstock is contacted with about 36-45 wt % sulfuric acid.

3. The method of claim 1, wherein the second portion of the feedstock is contacted with about 72 wt % sulfuric acid.

4. The method of claim 1, wherein the feedstock is dried prior to being contacted with sulfuric acid.

5. The method of claim 1, wherein the feedstock is washed with isopropanol prior to being contacted with sulfuric acid.

6. The method of claim 1, wherein the amount of glucose derived from cellulose is used to determine the amount of cellulosic ethanol derivable from a feedstock.

7. A method for measuring an amount of cellulose-derivable glucose in a feedstock comprising a mixture of starch and cellulosic components, comprising:
    (i) dividing the feedstock into a first portion and a second portion;
    (ii) contacting the first portion of the feedstock with about 30 to about 55 wt % sulfuric acid for about 1 hour, optionally at about 30° C., followed by diluting the first portion of the feedstock to 2 wt % sulfuric acid and continuing incubation for about 45 minutes under autoclave conditions;
    (iii) cooling the first portion of the feedstock and neutralizing acidity of the first portion of the feedstock with calcium carbonate;
    (iv) determining an amount of non-cellulose derivable glucose present in the first portion;
    (v) contacting the second portion of the feedstock with about 63-83 wt % sulfuric acid for about 1 hour at about 30° C. followed by diluting the second portion of the feedstock to 4 wt % sulfuric acid and continuing incubation for about 45 minutes under autoclave conditions;
    (vi) cooling the second portion of the feedstock and neutralizing acidity of the second portion of the feedstock with calcium carbonate; and
    (vii) comparing the amount of non-cellulosic-derivable glucose determined in first portion with the amount of total glucose determined in the second portion to determine the amount of cellulose-derivable glucose in the feedstock, where an increased amount of glucose in the total glucose in the second portion of the feedstock contacted with sulfuric acid in (v) compared the first portion of the feedstock contacted with sulfuric acid in (i) corresponds to cellulose-derivable glucose in the feedstock.

8. A method for measuring the amount of cellulose-derivable glucose in a feedstock comprising a mixture of starch and cellulosic components, said comprising:
    contacting a sample of feedstock with about 30 to about 55 wt % sulfuric acid for about 1 hour, optionally at about 30° C., followed by diluting the sample of the feedstock to 2 wt % sulfuric acid and continuing incubation for about 45 minutes under autoclave conditions;
    removing soluble material from the sample and retaining a solids fraction;
    contacting the solids fraction with about 63-83 wt % sulfuric acid for about 1 hour at about 30° C. followed by diluting the sample of the feedstock to 4 wt sulfuric acid and continuing incubation for about 45 minutes under autoclave conditions;
    determining an amount of glucose in the solids fraction which corresponds to cellulose-derivable glucose in the feedstock.

9. A method for measuring an amount of cellulose-derivable glucose in a feedstock comprising a mixture of starch and cellulosic components, comprising:
    (i) contacting a sample of the feedstock with about 30 to about 55 wt % sulfuric acid for about 1 hour, optionally at about 30° C., followed by diluting the sample of the feedstock to 2 wt % sulfuric acid and continuing incubation for about 45 minutes under autoclave conditions;
    (ii) removing soluble material from the sample of the feedstock and retaining a solids fraction;
    (iii) contacting the solids fraction with about 63-83 wt % sulfuric acid for about 1 hour at about 30° C. followed by diluting the solids fraction to 4 wt % sulfuric acid and continuing incubation for about 45 minutes under autoclave conditions;
    (iv) cooling the solids fraction contacted with sulfuric acid in (iv) and neutralizing acidity with calcium carbonate; and
    (v) determining an amount of glucose present in the solids fraction which corresponds to cellulose-derivable glucose in the feedstock.

10. The method of claim 9, wherein the sample of the feedstock is contacted with about 36-45 wt % sulfuric acid in (i).

11. The method of claim 9, wherein the sample of the feedstock is contacted with about 72 wt % sulfuric acid in (iii).

12. The method of claim 9, wherein the feedstock contains yeast cells and prior to step (iii) the remaining material is contacted with a lyticase enzyme at a temperature and for a time sufficient to release glucans from yeast present in the sample.

13. The method of claim 12, wherein after contacting with the lyticase the sample is separated into a solubles liquid fraction and a solids fraction and the solids fraction is washed to remove residual solubles prior to contacting with about 63-83 wt % sulfuric acid.

14. A method for measuring an amount of cellulose-derivable glucose in a feedstock comprising a mixture of starch and B-glucan and hemicellulose components, said method comprising:
   (i) contacting a sample of the feedstock with a 2 to 4-molar hydroxide base at a temperature of −5 to 5° C. for at least 10 minutes then adding a buffer to bring the sample to a pH allows for hydrolyzation using amyloglucosidase and a-amylase enzymes;
   (ii) contacting the feedstock with amyloglucosidase and an a-amylase at a temperature of 90 to 100° C. for a time sufficient to enzymatically hydrolyze at least 90% of the starch to glucose forming a first solubles fraction;
   (iii) separating the first solubles fraction from solids present in the feedstock and retaining a first separated solids fraction;
   (iv) determining the amount of non-cellulosic derivable glucose present in the first solubles fraction, which corresponds to starch derived glucose;
   (v) contacting the first separated solids fraction with sulfuric acid at a concentration of 63-83% at a temperature of 27-33°C for a time of 55-65 minutes forming a concentrated acid treated sample;
   (vi) diluting the sulfuric acid in the concentrated acid treated sample to 4% to form a diluted acid sample;
   (vii) incubating the diluted acid sample at temperature of 120-121° C. under autoclave conditions for a time sufficient to hydrolyze at least 90% of the cellulosic components initially present in the feedstock to glucose forming a second solubles liquid fraction;
   (viii) separating the second solubles fraction from a second solids fraction obtained from the diluted acid sample;
   (ix) determining an amount of glucose in the second solubles fraction which corresponds to cellulose-derivable glucose in the feedstock.

15. The method of claim 14, wherein the sample of the feedstock is contacted with about 72 wt % sulfuric acid in (v).

16. The method of claim 14, wherein the feedstock contains yeast cells, and wherein prior to step (v) the feedstock is contacted with a lyticase enzyme at a temperature of 45-55° C. for a time sufficient to hydrolyze at least 90% of yeast B-glucans in the sample.

17. The method of claim 14, wherein the feedstock is washed with an isopropyl alcohol prior to step (i).

18. The method of claim 14, wherein the first retained solids fraction is washed to remove residual solubles material prior to step (v).

\* \* \* \* \*

UNITED STATES PATENT AND TRADEMARK OFFICE
CERTIFICATE OF CORRECTION

PATENT NO. : 12,084,728 B2  
APPLICATION NO. : 17/286699  
DATED : September 10, 2024  
INVENTOR(S) : Kirstin Y. Nose Crotty et al.

Page 1 of 1

It is certified that error appears in the above-identified patent and that said Letters Patent is hereby corrected as shown below:

On the Title Page

Item (72) delete "Kristin Y. Nose Crotty"; and insert -- Kirstin Y. Nose Crotty --

Signed and Sealed this  
Twenty-sixth Day of November, 2024

Katherine Kelly Vidal  
*Director of the United States Patent and Trademark Office*